US007211067B2

(12) United States Patent
Hawk et al.

(10) Patent No.: US 7,211,067 B2
(45) Date of Patent: May 1, 2007

(54) ELONGATED MEDICAL DEVICE WITH FUNCTIONAL DISTAL END

(75) Inventors: Matthew Hawk, Otsego, MN (US); Scott Larson, St. Louis Park, MN (US); Timothy J. Mickley, Elk River, MN (US); Chad Harris, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 312 days.

(21) Appl. No.: 10/844,425

(22) Filed: May 13, 2004

(65) Prior Publication Data

US 2004/0210193 A1 Oct. 21, 2004

Related U.S. Application Data

(63) Continuation of application No. 10/379,591, filed on Mar. 6, 2003, now Pat. No. 6,767,338, which is a continuation of application No. 09/695,527, filed on Oct. 24, 2000, now Pat. No. 6,582,400.

(51) Int. Cl.
*A61M 5/178* (2006.01)

(52) U.S. Cl. ................................. 604/164.01

(58) Field of Classification Search .................. 604/22, 604/164.01, 164.02–164.09; 600/564–567; 606/167, 170

See application file for complete search history.

(56) References Cited

U.S. PATENT DOCUMENTS

| 4,427,014 A | * | 1/1984 | Bel et al. ..................... 600/564 |
| 4,662,371 A | * | 5/1987 | Whipple et al. ............. 606/170 |
| 4,740,195 A | | 4/1988 | Lanciano |
| 4,760,131 A | | 7/1988 | Sundsmo et al. |
| 4,790,311 A | | 12/1988 | Ruiz |
| 4,836,205 A | * | 6/1989 | Barrett ........................ 606/144 |
| 4,896,671 A | | 1/1990 | Cunningham et al. |
| 4,976,710 A | | 12/1990 | Mackin |

(Continued)

FOREIGN PATENT DOCUMENTS

DE    296 09 350 U 1    10/1996

(Continued)

OTHER PUBLICATIONS

Mirhoseini, et al., Abstract entitled "Transventricular Revascularization by Laser", Lasers in Surgery and Medicine, 2(2), 1982, 1 page.

(Continued)

*Primary Examiner*—Manuel Mendez
(74) *Attorney, Agent, or Firm*—Kenyon & Kenyon LLP

(57) ABSTRACT

An elongate medical device that may be used for performing medical procedures on a patient is provided. This elongate medical device may include a first member having an elongated configuration, a second member pivotally coupled to the first member at a pivot area of the first member, and a manipulation member extending through either a first lumen or a second lumen of the first member. The second member of this device may have a first region on one side of the pivot area and a second region on a different side of the pivot area. The medical device may also include a third member slidable within one of the lumens of the first member.

14 Claims, 19 Drawing Sheets

U.S. PATENT DOCUMENTS

| | | |
|---|---|---|
| 5,047,026 A | 9/1991 | Rydell |
| 5,093,877 A | 3/1992 | Aita et al. |
| 5,217,458 A * | 6/1993 | Parins .................... 606/48 |
| 5,261,889 A | 11/1993 | Laine et al. |
| 5,287,861 A | 2/1994 | Wilk |
| 5,352,198 A | 10/1994 | Goldenberg et al. |
| 5,358,485 A | 10/1994 | Vance et al. |
| 5,364,393 A | 11/1994 | Auth et al. |
| 5,370,675 A | 12/1994 | Edwards et al. |
| 5,380,316 A | 1/1995 | Aita et al. |
| 5,389,096 A | 2/1995 | Aita et al. |
| 5,403,311 A | 4/1995 | Abele et al. |
| 5,431,649 A | 7/1995 | Mulier et al. |
| 5,471,992 A * | 12/1995 | Banik et al. .................... 600/564 |
| 5,522,815 A | 6/1996 | Durgin, Jr. et al. |
| 5,551,427 A | 9/1996 | Altman |
| 5,569,462 A | 10/1996 | Martinson et al. |
| 5,591,159 A | 1/1997 | Taheri |
| 5,593,405 A | 1/1997 | Osypka |
| 5,607,405 A | 3/1997 | Decker et al. |
| 5,620,414 A | 4/1997 | Campbell, Jr. |
| 5,672,174 A | 9/1997 | Gough et al. |
| 5,681,308 A | 10/1997 | Edwards et al. |
| 5,683,366 A | 11/1997 | Eggers et al. |
| 5,697,882 A | 12/1997 | Eggers et al. |
| 5,700,259 A | 12/1997 | Negus et al. |
| 5,713,894 A | 2/1998 | Murphy-Chutorian et al. |
| 5,715,832 A * | 2/1998 | Koblish et al. .................... 600/564 |
| 5,725,521 A | 3/1998 | Mueller |
| 5,725,523 A | 3/1998 | Mueller |
| 5,810,836 A | 9/1998 | Hussein et al. |
| 5,823,971 A * | 10/1998 | Robinson et al. .................... 600/567 |
| 5,871,495 A | 2/1999 | Mueller |
| 5,935,119 A | 8/1999 | Guy et al. |
| 5,938,632 A | 8/1999 | Ellis |
| 5,957,900 A | 9/1999 | Ouchi |
| 6,039,727 A | 3/2000 | Javier, Jr. et al. |
| 6,042,581 A | 3/2000 | Ryan et al. |
| 6,045,565 A | 4/2000 | Ellis et al. |
| 6,053,877 A * | 4/2000 | Banik et al. .................... 600/566 |
| 6,053,911 A | 4/2000 | Ryan et al. |
| 6,053,924 A | 4/2000 | Hussein |
| 6,056,742 A | 5/2000 | Murphy-Chutorian et al. |
| 6,056,743 A | 5/2000 | Ellis et al. |
| 6,093,185 A | 7/2000 | Ellis et al. |
| 6,102,926 A | 8/2000 | Tartaglia et al. |
| 6,142,957 A * | 11/2000 | Diamond et al. .................... 600/567 |
| 6,156,029 A | 12/2000 | Mueller |
| 6,217,554 B1 | 4/2001 | Green |
| 6,238,406 B1 | 5/2001 | Ellis et al. |
| 6,350,914 B1 | 2/2002 | Eller et al. |
| 6,363,938 B2 | 4/2002 | Saadat et al. |
| 6,508,789 B1 | 1/2003 | Sinnott et al. |
| 6,547,761 B2 | 4/2003 | Liu |
| 6,582,400 B1 | 6/2003 | Hawk et al. |
| 6,673,060 B1 | 1/2004 | Fleming, III |
| 2001/0012918 A1 | 8/2001 | Swanson |

FOREIGN PATENT DOCUMENTS

| | | |
|---|---|---|
| DE | 195 37 084 A1 | 4/1997 |
| EP | 0 542 428 A | 5/1993 |
| WO | WO 96/35469 | 11/1996 |
| WO | WO 96/39963 | 12/1996 |
| WO | WO 97/18768 | 5/1997 |
| WO | WO 97/29803 | 8/1997 |
| WO | WO 97/32551 | 9/1997 |
| WO | WO 97/44071 | 11/1997 |
| WO | WO 98/05307 | 2/1998 |
| WO | WO 98/16157 | 4/1998 |
| WO | WO 98/17186 | 4/1998 |
| WO | WO 99/22655 | 5/1999 |
| WO | WO 00/015146 | 3/2000 |
| WO | WO 00/16704 | 3/2000 |

OTHER PUBLICATIONS

Gal, et al., Abstract entitled "Analysis of Photoproducts Free Radicals and Particulate Debris Generated . . . ", Lasers in Surgery and Medicine, 11(2) 1991, 1 page.

Isner, J., Abstract entitled "Right Ventricular Myocardial Infarction", JAMA, v259, n5, Feb. 5, 1988, 12 pages.

Pickering, et al., Abstract entitled "Proliferative Activity in Peripheral and Coronary Atherosclerotic Plaque . . . ", J. Clin. Invest., ISSN 0021-9738, Apr. 1993, 1 page.

Vineberg, et al., "Creation of Intramyocardial Pathways to Channel Oxygenated Blood Between Ventricular Arteriolar Zones", Canad. Med. Ass. J., vol. 96, Feb. 4, 1967, 3 pages.

Vineberg, A., "Results of 14 Years' Experience in the Surgical Treatment of Human Coronary Artery Insufficiency", Canad. Med. Ass. J., vol. 92, Feb. 13, 1965, 8 pages.

Vineberg, et al., "The Ivalon Sponge Procedure for Myocardial Revascularization", Surgery, vol. 47, No. 2, Feb. 1960, pp. 268-289.

Vineberg, et al., "Treatment of Acute Myocardial Infarction by Endocardial Resection", Surgery, vol. 57, No. 6, Jun. 1965, pp. 832-835.

Walter, et al., "Treatment of Acute Myocardial Infarction by Transmural Blood Supply from the Ventricular Cavity", European Surgical Research, 3:130-138 (1971).

Khazei, et al., "Myocardial Canalization", The Annals of Thoracic Surgery, vol. 6, No. 2, Aug. 1968, pp. 163-171.

Hershey, et al., "Transmyocardial Puncture Revascularization", Geriatrics, Mar. 1969, pp. 101-108.

Press Release dated Oct. 21, 1965, "Doctor's Demonstrate Proof of Blood Flow Through Open TMR Channels Created with PLC System . . . ", 1 page.

Press/News Release dated Oct. 10, 1996, "Texas Fieart Institute Presents Study Comparing the Use of CO2 . . . ", 1 page.

Goldman, et al., "Nonoperative Portacaval Shunt in Swine", Investigate Radiology, vol. 25, No. 5, May 1990, 5 pages.

Schumacher, et al., "Induction of Neoangiogenesis in Ischemic Myocardium by Human Growth Factors", Clinical Investigation and Reports, Dec. 1, 1967, 6 pages.

Article entitled "Gene therapy improves leg circulation—next step heart?", 70th Scientific Sessions, published on or before Nov. 2, 1998, 2 pages.

Winslow, R., Genetic Techniques Succeed in Treating Patients with Obstructed Blood Vessels, The Wall Street Journal, published on or before Nov. 2, 1998, 2 pages.

Kolata, G., "Gene Therapy Gives Blood a Path Around Leg Blockages, Researchers Say", The New York Times, Nov. 10, 1997, 2 pages.

Mack, et al., "Cardiopulmonary Support and Physiology", The Journal of Thoracic and Cardiovascular Surgery, vol. 115, No. 1, Jan. 1998, 10 pages.

European International Search Report, Aug. 2, 2002.

* cited by examiner

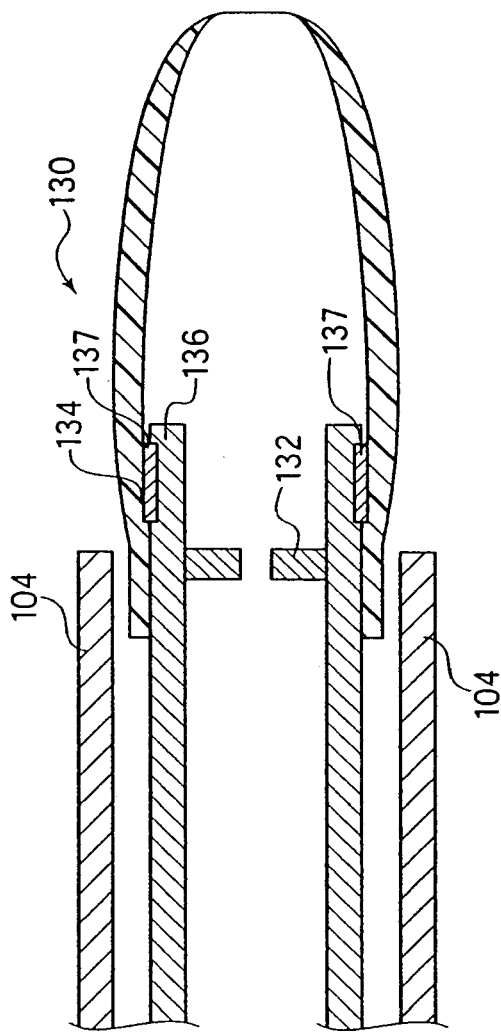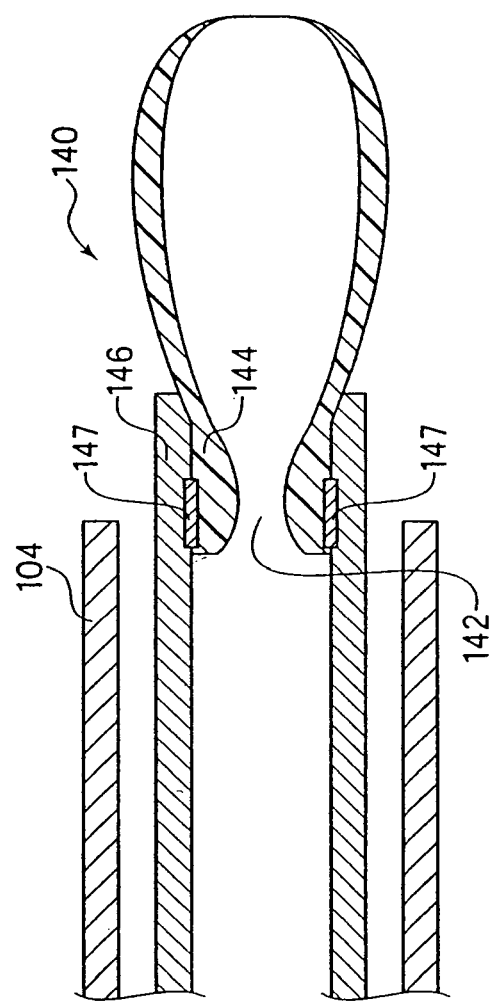
FIG. 5
FIG. 6

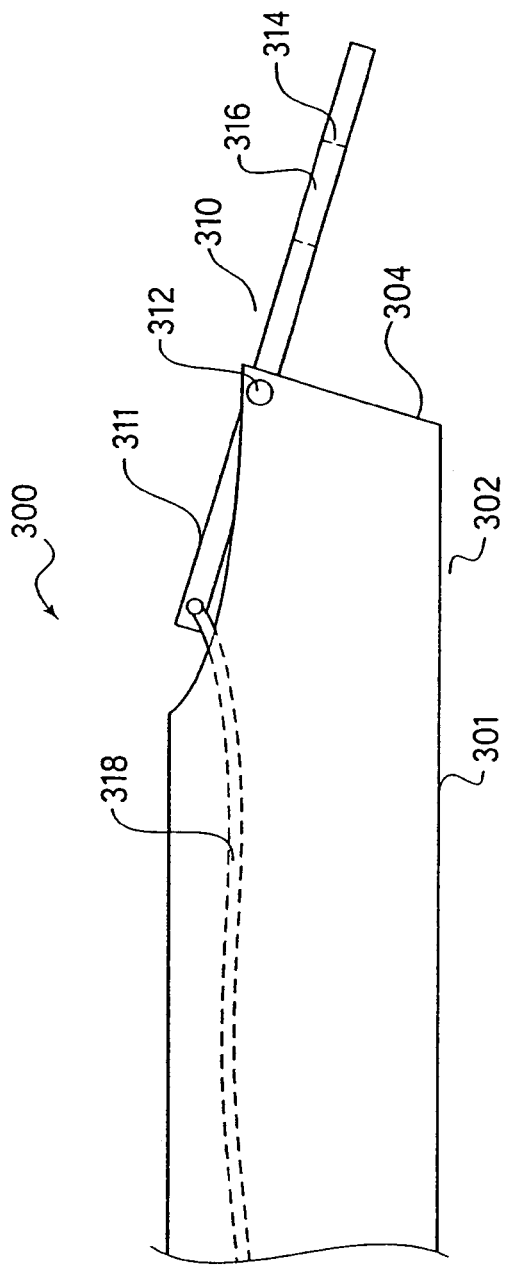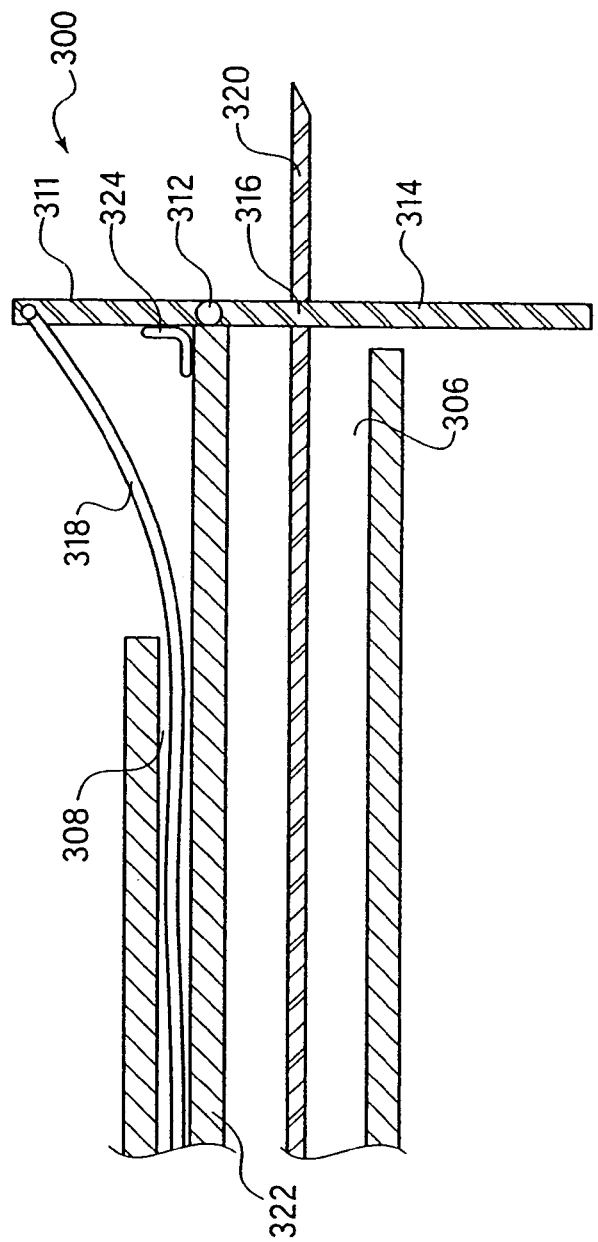

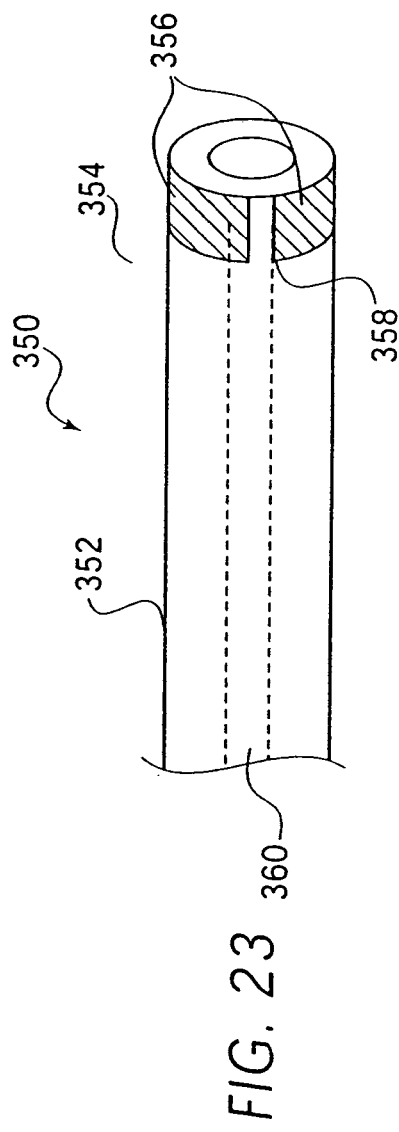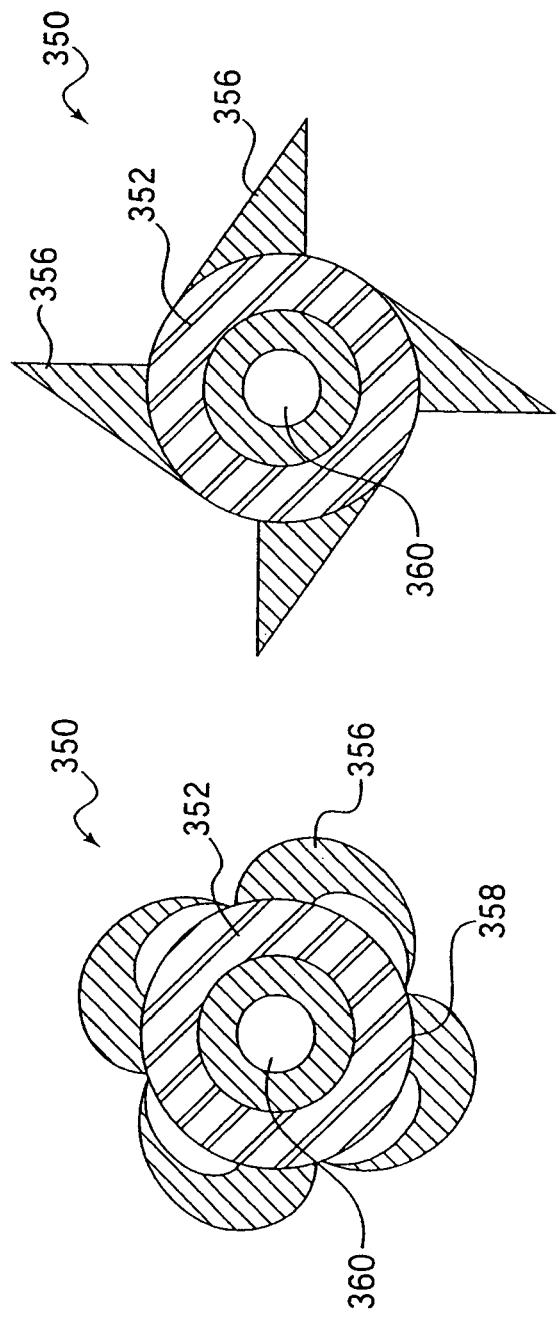
FIG. 23
FIG. 24
FIG. 25

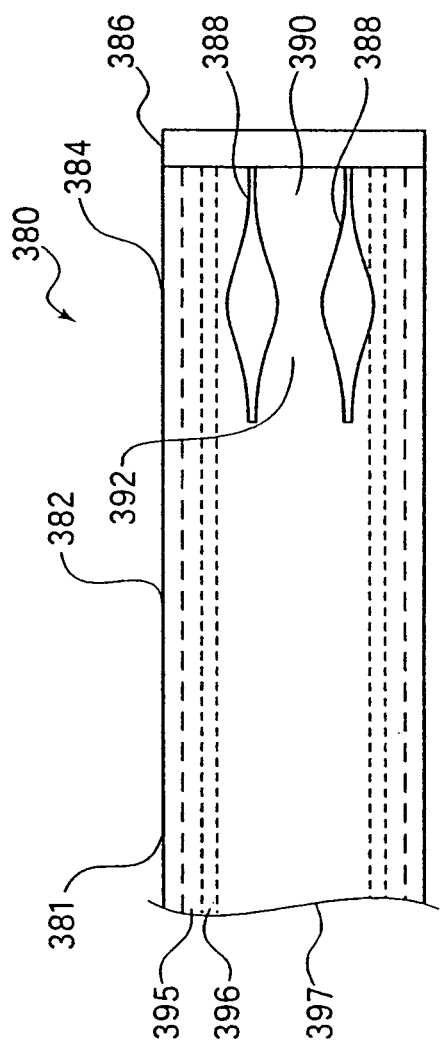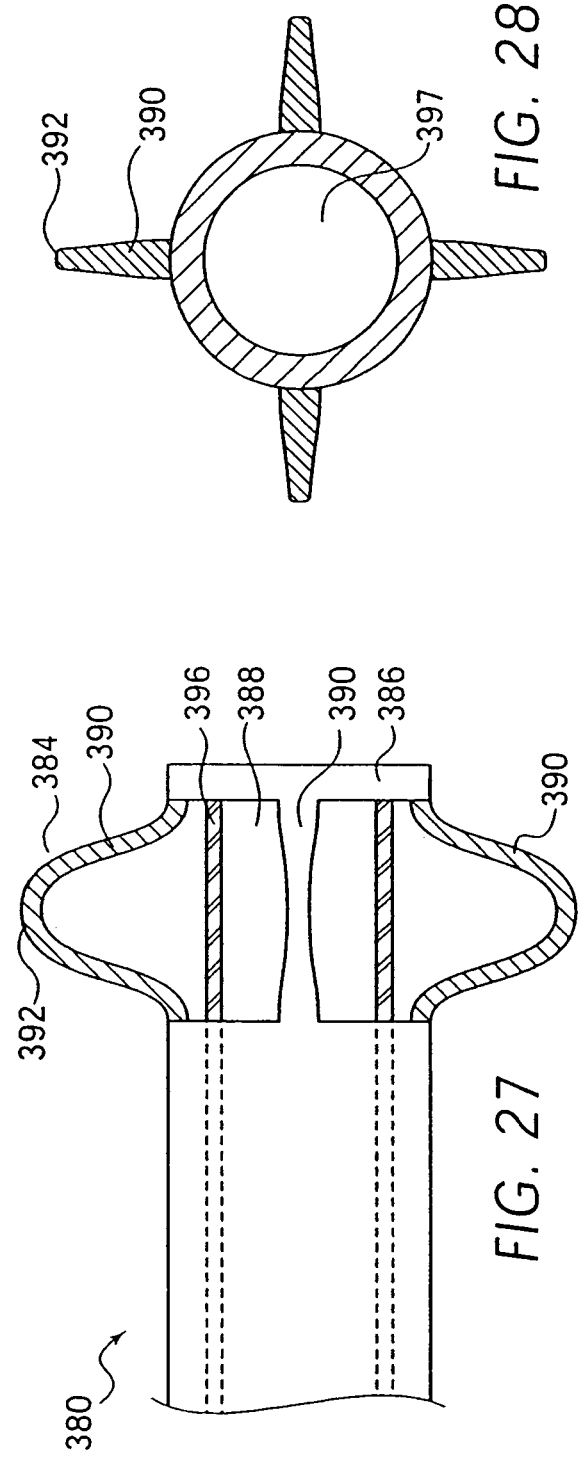

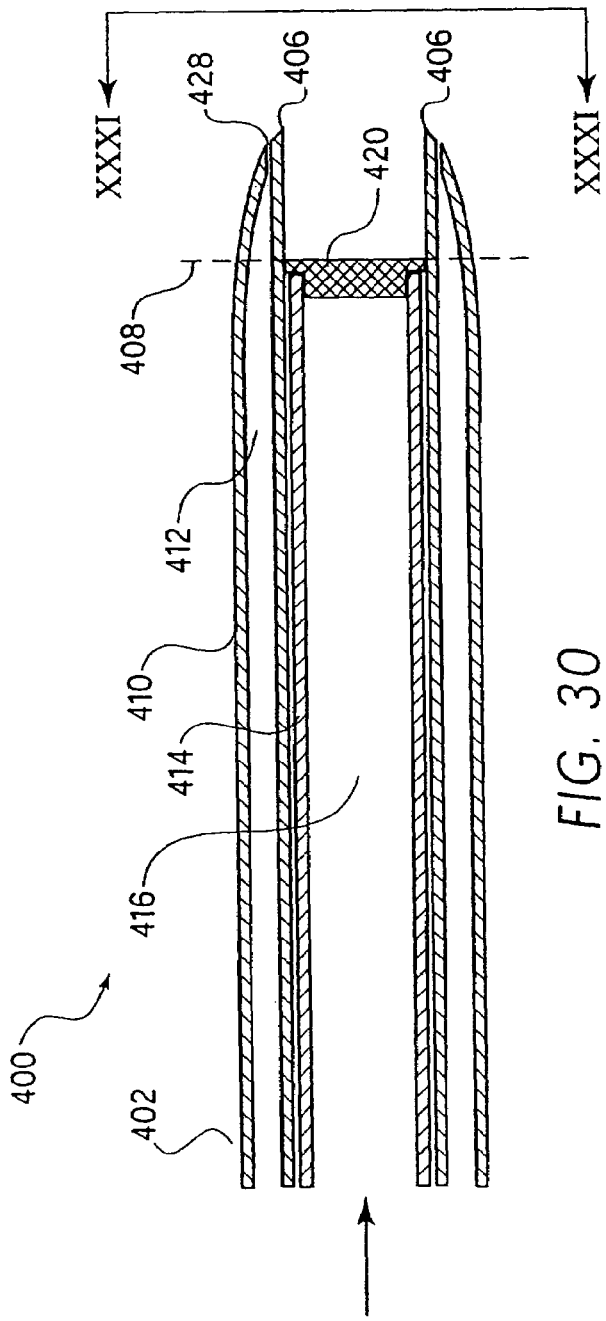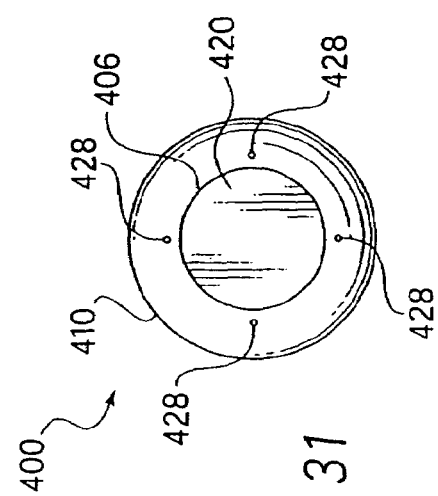
FIG. 30
FIG. 31

ELONGATED MEDICAL DEVICE WITH FUNCTIONAL DISTAL END

CROSS-REFERENCE TO RELATED APPLICATIONS

This application is a Continuation of application Ser. No. 10/379,591, filed Mar. 6, 2003, now U.S. Pat. No. 6,767,338 which is a Continuation of application Ser. No. 09/695,527, filed Oct. 24, 2000, now U.S. Pat. No. 6,582,400 both of which are included herein in their entirety by reference.

FIELD OF THE INVENTION

The claims of the present invention are directed towards medical devices. More specifically, the claims of the present invention are related to catheters, endoscopes, and other medical devices with function distal ends that may be used to perform medical procedures within the body of a patient.

BACKGROUND OF THE INVENTION

A number of techniques are available for treating cardiovascular disease such as cardiovascular bypass surgery, coronary angioplasty, coronary atherectomy, and stent placement. These techniques are generally performed to bypass or open lesions in coronary vessels to restore patency and increase blood flow to the heart muscle. In some patients, the number of lesions are so great, or the locations so remote in the coronary vasculature, that restoring coronary artery blood flow to the heart is difficult. Transmyocardial revascularization (TMR), also known as percutaneous myocardial revascularization (PMR), has been developed as an alternative to these techniques which are directed to bypassing or removing lesions.

Heart muscle may be classified as healthy, hibernating, and "dead." Dead tissue is not dead but is scarred, no longer contracting, and no longer capable of contracting even if adequately supplied with blood. Hibernating tissue is not contracting muscle tissue but is capable of contracting again, provided it is once more adequately supplied with blood. PMR is performed by wounding the myocardium of the heart, often forming and leaving patent holes, and sometimes injecting angiogenic substances in the process.

PMR was inspired in part by observations that reptilian hearts are largely supplied by blood directly from within the heart chambers. In contrast, mammalian hearts are supplied by blood pumped from the heart, through the aorta, and back to the heart muscle through the coronary arteries. Positive results have been observed in some patients receiving PMR treatments. The positive results may be due in part to blood being perfused into the myocardium from within the heart chambers through holes into the myocardium. The positive results are believed to be due in part to a wound healing response of the myocardium which includes formation of new blood vessels in the heart wall, which are believed to connect with the heart chamber interior and/or other coronary blood vessels. The PMR procedure can include cutting into the myocardium with therapeutic tips or burning holes with therapeutic tips having laser or radio-frequency current tips. PMR therapeutic tips can also be used to inject angiogenic substances such as growth factors or genes selected to induce angiogenesis.

The PMR procedure generally involves insertion of a therapeutic tip such as a sharp cutting tip into the heart chamber or chambers selected for treatment. The cutting tip and associated inner shaft can be guided into the chamber within a guide catheter, which may have been inserted into the vasculature a long distance from the heart. After the inner shaft distal end exits the guide catheter, the cutting tip is preferably steered to several positions for formation of several holes in a pattern across the endocardium. In order to steer the inner shaft and cutting tip, an outer shaft or tube is sometimes disposed coaxially about the inner shaft and within the guide catheter. The outer tube can have structural features at the distal end for bending to various angles to reach various locations in the heart wall. The outer tube and inner shaft can be cooperatively advanced to bring the cutting tip into contact with the heart wall.

To allow passage through the guide catheter, the outer tube should have a sufficiently small radial or transverse profile over its length. As with many catheter devices, a small profile is desirable to allow passage through tortuous and narrow vessels. At the outer tube distal end, however, a small profile can also mean a small profile presented to the heart wall when inserting a cutting tip. It may be desirable to bring the outer tube very close or even into contact with the heart wall. While inserting a cutting tip into the heart wall may be desirable, inserting the larger outer tube distal end into the heart wall may be undesirable.

What is desirable is an improved guide device for steering inner shaft cutting tips into position within the heart myocardium. The improved guide device would preferably include a distal end having a small profile for passage through a guide catheter, yet having a larger profile for presentation to the heart inner wall to limit undesirable penetration by the guide device distal end.

SUMMARY OF THE INVENTION

The present invention includes devices for performing percutaneous myocardial revascularization (PMR) that can lessen the likelihood of a shaft distal end penetrating undesirably into the myocardium. In one application, PMR devices are used to penetrate the endocardium and myocardium to a controlled depth. One group of devices according to the present invention includes an inner shaft having a therapeutic tip, for example, a distal cutting tip. The inner shaft can be disposed within an outer tube or shaft lumen, and the outer shaft can be disposed within the lumen of a guide catheter. Preferably, the myocardium. is penetrated by the cutting tip of the inner shaft but not by any larger profile outer shafts or tubes disposed about the inner shaft. The outer shaft distal region preferably has a first configuration having a small radial extent or profile allowing disposition of the outer shaft within a small guide catheter. The outer shaft distal region preferably also has a second configuration having a larger radial extent or profile for presentation against the endocardium. While having the larger profile, the outer tube distal end has increased resistance to penetrating the heart wall. The larger surface presented to the heart wall while in the radially expanded position forms a more atraumatic distal end for the outer tube distal end.

The outer tube distal end can have an atraumatic distal hood or tip that is formed of an elastic material that can be benignly forced against an obstacle such as the heart chamber inner wall, the endocardium. The atraumatic hood allows passage of the therapeutic tip therethrough to contact the heart wall. The atraumatic hood preferably has a sufficiently small profile so as to fit within an enclosing guide catheter in a first configuration. In one embodiment, the atraumatic hood is sufficiently elastic to longitudinally foreshorten and radially expand to attain a larger profile or radial extent when forced against the endocardium. The radially enlarged hood presents a larger transverse surface area to the heart wall and inhibits penetration of the heart wall by the outer shaft distal end. In one embodiment, the atraumatic hood has a bulbous shape and has a distal-most orifice for receiving the cutting tip of a slidably disposed inner therapeutic shaft.

One outer shaft atraumatic tip includes a distally disposed elastic member having a first, constrained configuration, and a second, unconstrained configuration. In a constrained configuration, which may occur when the tip is constrained within an enclosing guide catheter, the tip has a radial extent or profile that fits within the guide catheter. In an unconstrained configuration, the tip can expand to a larger radial extent or profile, where the radial extent is preferably larger than the outer diameter of the guide catheter. One atraumatic tip includes an elastomeric disk or washer transversely disposed to the longitudinal axis of the catheter. Another atraumatic tip includes several radially disposed segments or arms. In use, the atraumatic tip can expand radially outward when advanced from a guide catheter, and can radially contract when retracted back within the guide catheter.

Another outer shaft atraumatic distal end or stop includes a spring wound about the outside of the outer shaft distal region. The spring preferably has a constrained configuration when contained within an enclosing guide catheter. When advanced distally from the guide catheter, the spring preferably expands radially to a second, unconstrained configuration having a larger profile. The larger profile can present a hindrance to penetration of the endocardium by the distal end of the outer shaft. After use of any inner therapeutic shaft, the outer shaft can be retracted within a guide catheter, again constraining the distal spring and reducing the radial extent. In one embodiment, the spring is formed as a helical coil. In another embodiment, the spring is formed as a ribbon or clock spring disposed about a relatively short length of the outer shaft.

One device outer shaft includes an atraumatic distal region formed as an inflatable member having a small, uninflated profile and a large, inflated profile. The shaft can include an inflation lumen and the inflatable member can include an inflatable balloon having an interior in fluid communication with the inflation lumen. The distal inflatable member can be inserted uninflated within a guide catheter for delivery to a target site such as the endocardium. After advancing the distal inflatable member from a guide catheter, inflation fluid can be supplied through the inflation lumen and into the inflatable member, thereby increasing the radial extent of the inflatable member. The inflated member or balloon can present a larger distal transverse surface area, which presents an inhibition to penetration of the endocardium by the outer shaft distal end. One device has a dual lumen shaft with side-by-side lumens. Another device has an inflation lumen coaxially disposed about an inner lumen which can be used for delivery of a therapeutic inner shaft.

One device has a distal cross member having a first, transverse orientation, and a second, more longitudinal orientation. The cross member is preferably pivotally mounted to a distal-most portion of the outer tube. The cross member can have a first arm for attachment to an elongate manipulation member and a second, opposite arm having an opening for allowing passage of a therapeutic inner shaft through the transversely disposed cross member. In one embodiment, the cross member is biased to remain in a substantially transverse orientation to the longitudinal axis of the outer tube. In one embodiment, the attached cross member arm can be either pushed or pulled with the elongate manipulation member. In some embodiments the elongate manipulation member is capable of effectively pulling the cross member to a transverse position, but not of pushing the cross member arm to a smaller profile, more longitudinal orientation. In other embodiments, the elongate manipulation member is capable of both pushing and pulling the cross member between small and large profile orientations.

In yet another embodiment, the outer tube has distally disposed wings or fins having a first, closed position, and a second, open position. In the closed position, the wings can lie closely about the outer tube distal region outer walls, presenting a small transverse profile. In the open position, the wings can extend radially outward, presenting a large transverse profile. The wings can be biased to expand to the larger profile configuration when unconstrained by a guide catheter. In one embodiment, the wings are formed of a shape memory material, for example Nitinol, and expand to the larger profile configuration when warmed to body temperature. In use, the wings expand to present a large profile to the endocardium or other surface. The wings can be forced to contract when the outer shaft distal end is retracted within a guide catheter having a smaller inside diameter than the radial extent of the distal wings.

In still another embodiment, the outer tube has a distal region which can be followed distally by a distal end which can be terminated more distally by a distal-most portion. The distal end can include an outer tube wall region having several longitudinally disposed slits or slots defining wing regions therebetween. The wing regions can include preferential folding locations. An inner tube or shaft can be slidably and coaxially disposed within the outer tube and secured to the outer tube distal-most portion. The PMR device having the inner and outer tubes can be distally advanced from a guide catheter and the inner tube moved proximally relative to the outer tube, thereby applying a proximal pulling force on the outer tube distal-most portion. The applied force can force the longitudinal wings between the longitudinal slots to buckle and splay radially outward, longitudinally foreshortening the outer tube distal end in the process. The radially outwardly splayed wings can present a larger radial extent or profile to the endocardium and inhibit penetration of the endocardium by the outer tube. After use, the inner tube can be advanced relative to the reduced profile device and retracted within a guide catheter.

In another embodiment a therapeutic catheter includes an outer tube having a distal region, a distal end, a tube wall, and a first lumen within the outer tube. The outer tube distal end is preferably sufficiently sharp to penetrate into the endocardium. A stop can be disposed within the outer tube, defining a smaller inside diameter region in a proximal portion of the outer tube distal region. A plug disposed within the outer tube first lumen distal region preferably has a maximum outer dimension too large to allow proximal movement past the stop. When the sharp distal end penetrates into the myocardium, the penetration is limited by the myocardium contacting the plug, which can in turn be contacting the stop or shoulder. The stop can be an annular stop, defined by an integrally formed annular stop in one embodiment and by the distal end of an inserted inner tube in another embodiment.

In one therapeutic catheter for increasing myocardial blood perfusion, the outer tube wall has at least one substance delivery lumen disposed within and at least one injection port disposed near the outer tube distal end. In another therapeutic catheter an inner tube has a substance delivery lumen and a distal end, the inner tube being disposed within the outer tube. A plug having a lumen therethrough for receiving the inner tube can be slidably disposed within the outer tube, such that the inner tube distal end forms a distal shoulder for limiting proximal travel of the plug. In one embodiment, the inner tube distal end is sufficiently sharp to penetrate into the myocardium and extends distally past the plug when the plug abuts the shoulder.

BRIEF DESCRIPTION OF THE DRAWINGS

FIG. 5 is a fragmentary, longitudinal cross-sectional view of a PMR device extending from a guide catheter and having an elastically radially expandable atraumatic tip bonded to the outside of PMR device outer tube;

FIG. 6 is a fragmentary, longitudinal cross-sectional view of a PMR device extending from a guide catheter and having an elastically radially expandable atraumatic tip bonded to the inside of the PMR device outer tube;

FIG. 18 is a fragmentary, longitudinal side view of a PMR device having a distal, atraumatic pivotally mounted cross member, with a manipulation member drawn in phantom within the PMR device outer tube;

FIG. 19 is a fragmentary, longitudinal cross-sectional view of the PMR device of FIG. 18 having the distal cross member in a transverse position;

FIG. 23 is a fragmentary, perspective view of a PMR device outer tube having expandable distal wings in a contracted configuration;

FIG. 24 is an end view of the wings of the device in FIG. 23;

FIG. 25 is an end view of the wings of the device in FIG. 23 in an expanded configuration;

FIG. 26 is a fragmentary, perspective view of a PMR device having a slidable, coaxially disposed inner tube within an outer tube having a distal. end with longitudinal slits;

FIG. 27 is a fragmentary, perspective view of the outer tube of the device of FIG. 26 having the inner tube retracted and the distal end expanded to form an atraumatic tip;

FIG. 28 is an end view of the outer tube of FIG. 27 in the expanded configuration;

FIG. 30 is a fragmentary, longitudinal cross-sectional view of the PMR device of FIG. 29, the sharp distal end shown penetrating the endocardium up to the hood stop now abutting the inner tube distal end;

FIG. 31 is an end view of the PMR device of FIG. 29, illustrating the hood stop within the outer tube, with injection holes shown in the outer tube distal end;

DETAILED DESCRIPTION OF THE INVENTION

Figure 1:
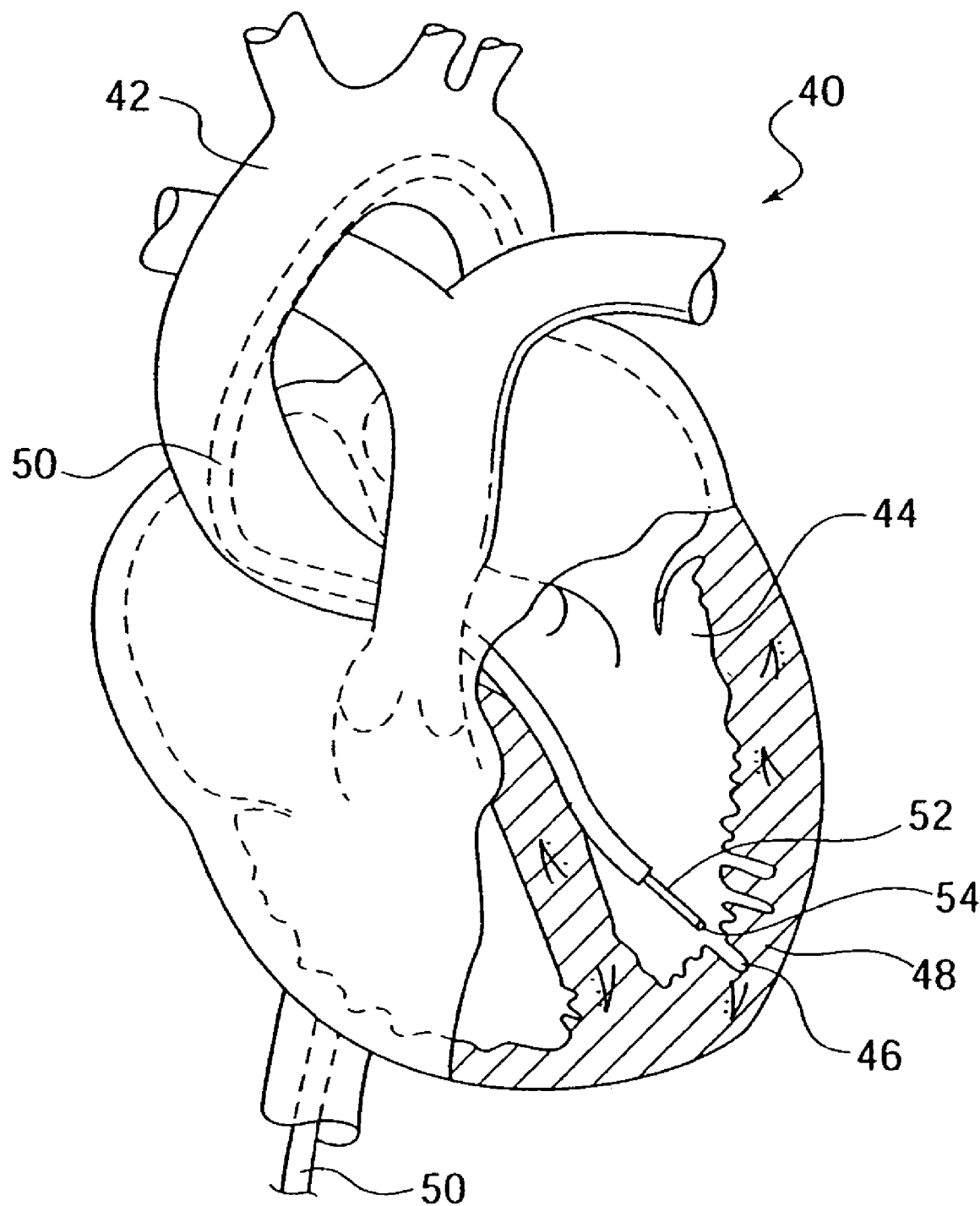
FIG. 1 is a cutaway, perspective view of a human heart having a PMR therapeutic tip catheter disposed within a guide catheter in the left ventricle.

FIG. 1 illustrates a human heart 40 having a guide catheter 50 inserted through the aortic arch 42 and into the left ventricle 44. Guide catheter 50 is shown having a therapeutic catheter 52 extending therethrough terminating in a therapeutic catheter therapeutic tip 54. Therapeutic tip 54 can be used to form a plurality of holes 46 in left ventricle wall 48. Therapeutic tip 54 can be used to form holes in order to stimulate a healing, response as well as to inject angiogenic substances such as VEGF and other factors well-known in the art. As can be seen from inspection of FIG. 1, the depth of holes 46 in left ventricle wall 48 are important as the holes should optimally not penetrate through the entire wall thickness of the myocardium. As further explained below, therapeutic catheter 52 is often not directly disposed within guide catheter 50. In particular, therapeutic catheter 52 may be disposed within an enclosing outer tube coaxially disposed between therapeutic catheter 52 and guide catheter 50.

Figure 2:
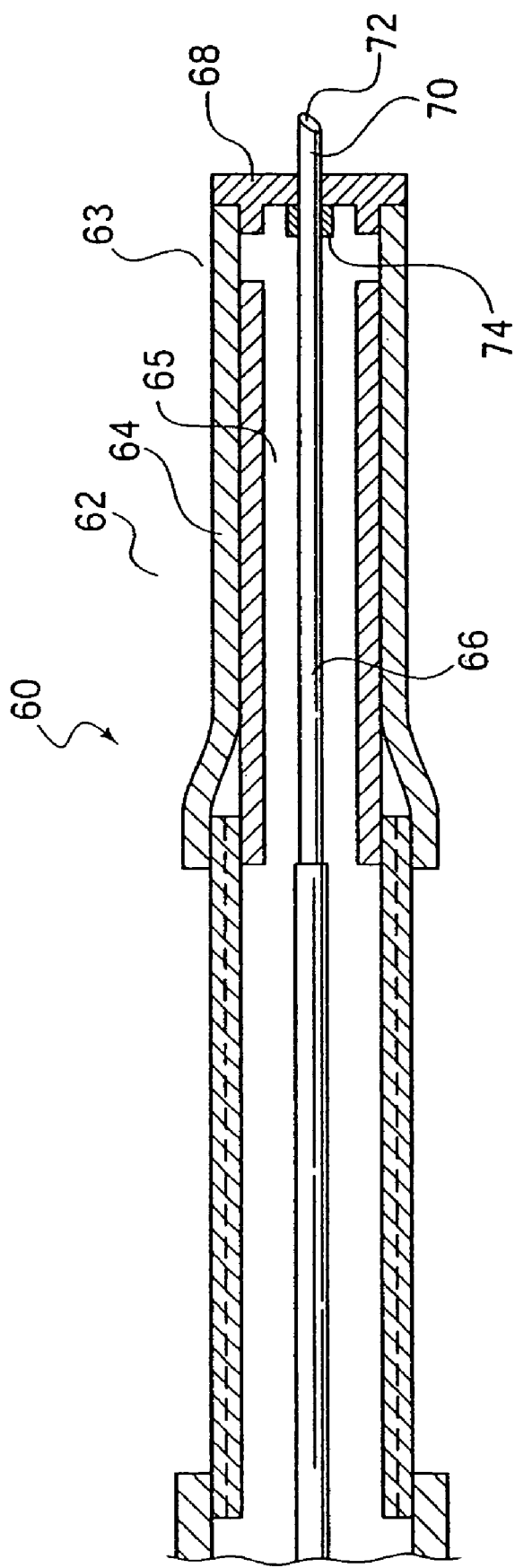
FIG. 2 is fragmentary, longitudinal, cutaway view of a PMR device having an outer tube and an inner therapeutic shaft with therapeutic tip disposed therein.

FIG. 2 illustrates generally a PMR device 60, including a distal. end 63 and a distal portion 62 having an outer tube 64 having a lumen 65 therein. Device 60 is an example of a PMR device suitable for inclusion of the present invention. In particular, the distal profile of device 60 may be configurably expanded by incorporating various embodiments of the present invention. A second, inner tube or shaft 66 is disposed within lumen 65 extending to a therapeutic tip region 70 terminating in a sharp, cutting end 72 in the embodiment illustrated. Inner tube 66 may be slidably disposed within an outer tube 64. The embodiment illustrated further includes a tip 68 terminating outer tube 64. Inner tube 66 may be formed of a hypotube material and may include a swage collar 74 to limit travel of inner shaft 66. As further discussed below, outer tube distal end 63 and/or distal tip may have the profile or radical extent configurably increased.

Figure 3:
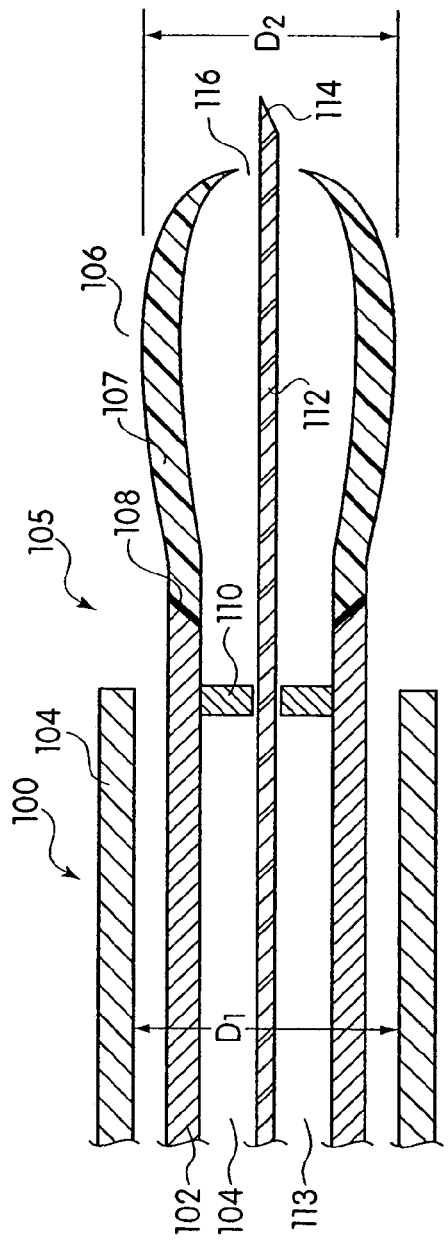
FIG. 3 is a fragmentary, longitudinal cross-sectional view of a PMR device extending from a guide catheter and having an elastically radially expandable atraumatic tip bonded to the PMR device outer tube.

FIG. 3 illustrates a device 100 including a guide catheter 104 having a PMR device 105 disposed therein. As can be seen from inspection of FIG. 2, PMR device 105 has a maximum relaxed outer diameter of D2, which may be compared to the inside diameter of guide catheter 104, D1. The relatively small outer diameter or profile of device 105 allows the device to fit within guide catheter 104. Device 105 includes an outer wall or tube 102 and a distal region 106. Distal region 106 includes an outer wall 107 bonded at 108 to outer tube 102. An inner shaft or therapeutic catheter 112 is disposed within a lumen 113 within outer tube 102. Therapeutic catheter 112 terminates distally in a therapeutic catheter therapeutic tip 114. Therapeutic tip 114 may have a sharp cutting end and can include means for injecting substances into the heart wall. In one embodiment, inner shaft 112 is a tube having a lumen therethrough. Therapeutic catheter 112 may be seen to extend through a brush or flange region 110. Distal region 106 terminates distally in a distal orifice 116. As can be seen from inspection of FIG. 3, the wall thickness of distal region 106 is thinner distally than proximally. In some embodiments, distal orifice 116 is not formed until the distal-most region of distal region 106 is perforated by therapeutic tip 114. This perforation can occur as the result of advancing a slidably disposed cutting tip through the distal-most region and/or by pressing the distal-most region against an obstacle such as the heart wall.

Figure 4:
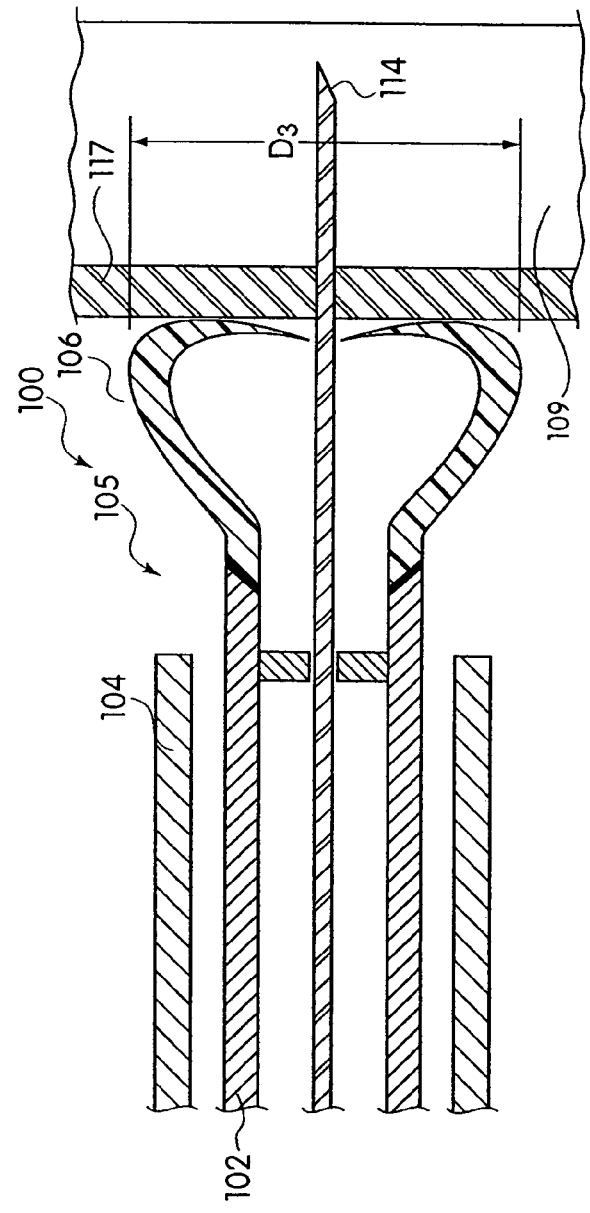
FIG. 4 is a fragmentary, longitudinal cross-sectional view of the device of FIG. 3 forced against the endocardium, with the inner shaft penetrating the myocardium and the atraumatic tip radially expanded.

FIG. 4 illustrates device 105 disposed against a portion of the heart wall 117. Therapeutic tip 114 may be seen to have penetrated well into the heart myocardium 109. As distal region 106 is forced against the heart wall, the maximum radial extent or profile of the device may be seen to increase, as indicated at D3. FIG. 4 illustrates a configuration in which device 105 has not been fully pressed against the heart wall. As illustrated by FIG. 4, the bulbous distal region 106 is splayed radially outward by compression against the heart wall. In some embodiments, the depth of penetration of therapeutic tip 114 is limited primarily by the outward splaying of distal region 106. In some embodiments, therapeutic catheter 112 may be relatively fixed within outer tube 102. In such embodiments, the travel of therapeutic tip 114 into the heart wall is limited by the geometry of distal region 106.

As illustrated by FIG. 4, the outer profile presented by the compressed or splayed distal region 106 is substantially greater than the profile presented within the guide catheter. FIG. 4 thus illustrates device 106 having only a small profile while within the guide catheter and a larger profile when presented against the heart wall, thereby presenting a travel limiting, outwardly splayed larger profile surface. Distal region 106 can be formed of a polymeric material, preferably one having sufficient elastomeric properties so as to return to the configuration illustrated in FIG. 3 after being splayed outward against the heart wall, as illustrated in FIG. 4.

FIG. 5 illustrates another embodiment device 130 in which the distal region includes an outer distal region wall 134 disposed over the outside of a tube wall 136 and bonded thereto at 137. As in FIG. 3, device 130 includes a brush or flange region 132 disposed within 134. FIG. 6 illustrates yet another embodiment device 140 in which the distal region walls 144 are disposed within outer tube wall 146 and bonded thereto at 147. In the embodiment illustrated, the distal region walls 144 are narrowed in throat region 142 which can serve as a brush for receiving a therapeutic catheter tip therethrough. As can be seen from inspection of FIGS. 3–6, the distal regions of the devices are radially expanded and longitudinally foreshortened by contact with the heart wall. The force of compression against the heart wall is the primary causative factor in expanding the distal regions of the devices radially.

Figure 7:
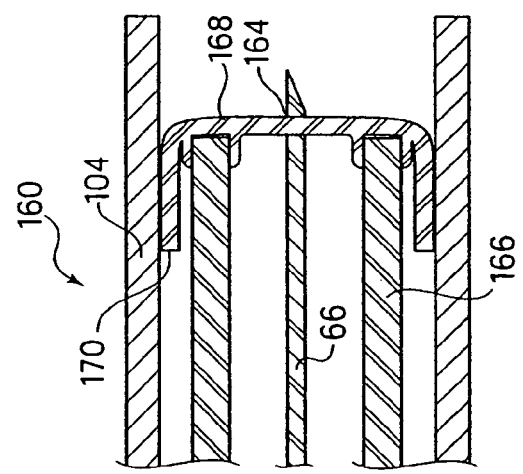
FIG. 7 is a fragmentary, longitudinal cross-sectional view of a PMR device disposed within a guide catheter and having an elastically radially expandable atraumatic distal flange constrained within the guide catheter.

FIG. 7 illustrates yet another PMR device 160 having an outer tube 166 terminating in a distally disposed flange 168. Flange 168 includes an orifice 164 therethrough for receiving therapeutic catheter 66. Flange 168 includes outward extent 170, illustrated as bent alongside outer tube 166, within guide catheter 104. While constrained within guide catheter 104, flange 168 has a small transverse profile.

Figure 8:
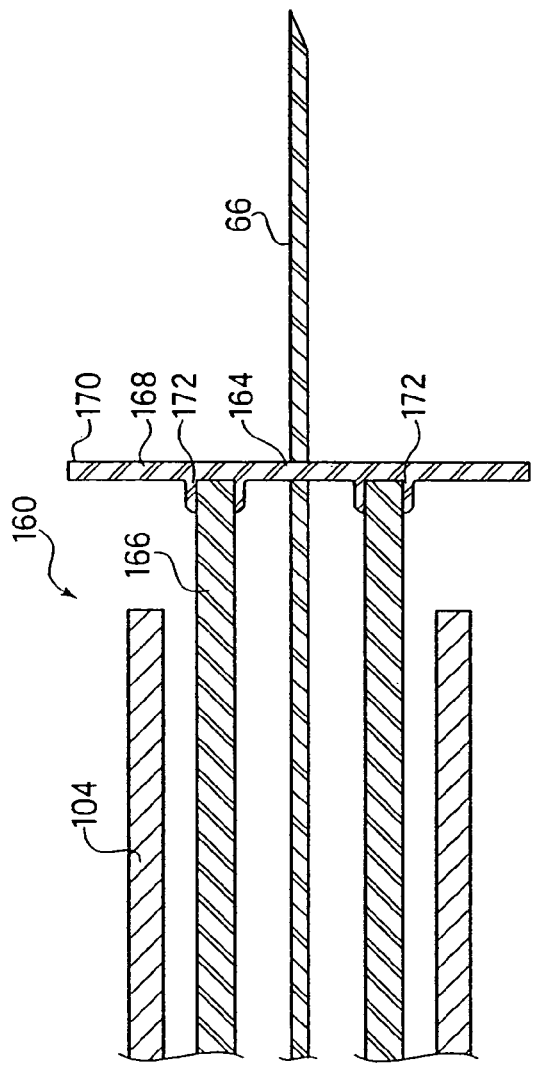
FIG. 8 is a fragmentary, longitudinal cross-sectional view of the PMR device of FIG. 7 extending from within the guide catheter and having the expandable atraumatic distal flange radially extended.
Figure 9:
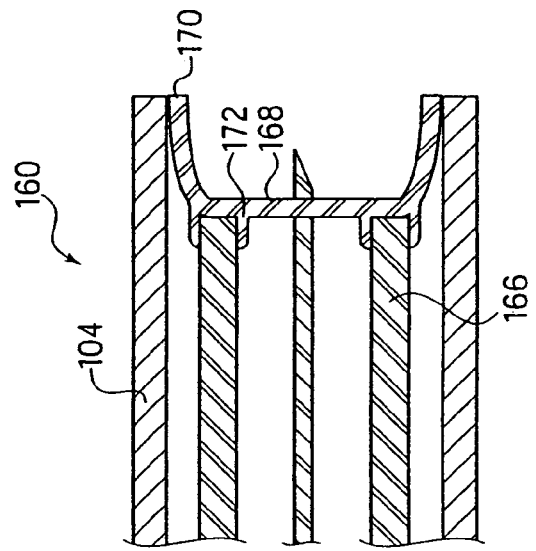
FIG. 9 is a fragmentary, longitudinal cross-sectional view of the PMR device of FIG. 7 retracted within the guide catheter and having the atraumatic distal flange radially constrained within the guide catheter.

Referring now to FIG. 8, PMR device 160 has been distally forced from the constraint of guide catheter 104. Outermost extent 170 of flange 168 may be seen to have expanded radially. Flange 168 now has a radial extent or profile larger than the radial extent or profile of guide catheter 104. Flange 168 may be formed of an elastomeric material such as siliconized rubber, Tecoflex, Tecothane, or 80A Pellathane. Flange 168 may be formed of soft polymers with or without radiopaque loading or coating. In one embodiment, flange 168 includes mounting or bonding arms 172 bonded to outer tube 166. When pressed against the heart wall, flange 166 can present a very large profile for reducing the likelihood of outer tube 166 penetrating into the heart wall. After use, as illustrated FIG. 9, outer tube 166 and attached flange portion 168 can be retracted proximally back within guide catheter 104. In this configuration again, flange portion 168 has a reduced outer profile or radial extent. This allows PMR device 160 to be retracted through the guide catheter.

Figure 10:
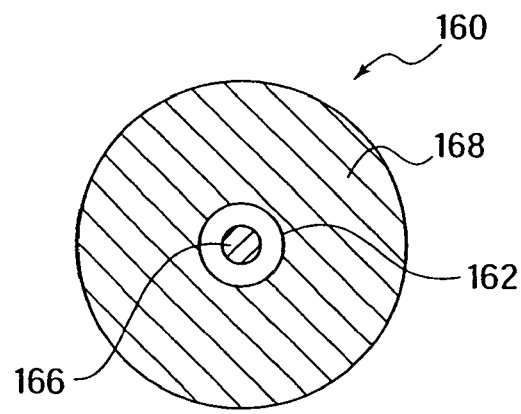
FIG. 10 is an end view of the PMR device atraumatic distal flange of FIG. 8.
Figure 11:
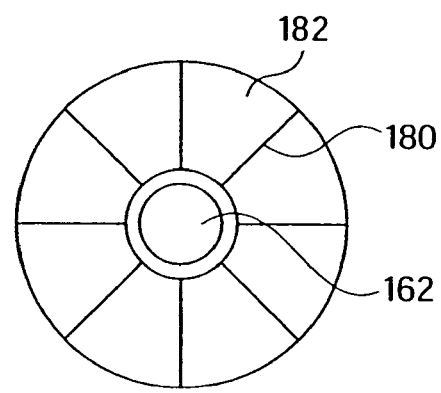
FIG. 11 is an end view of a PMR device atraumatic distal flange having radial slits.
Figure 12:
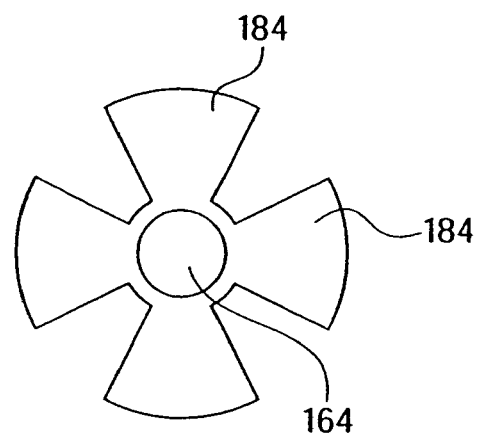
FIG. 12 is an end view of a PMR device atraumatic distal flange having radial arm segments.

FIG. 10 illustrates a transverse, end view of one embodiment of PMR device 160, illustrating distal flange portion 168. In the embodiment illustrated, distal flange portion 168 is a substantially continuous washer having orifice 162 therethrough. Referring now to FIG. 11, a distal flange portion is formed of a plurality of slits 180 defining a plurality of segments 182 therebetween. FIG. 12 illustrates yet another embodiment of a distal flange portion having a plurality of separated arms 184 disposed about a central orifice 164. As can be seen from inspection of FIGS. 7 through 12, the expandable tip portion operates by having a distal flange which is biased to assume a large radial extent or profile when in the unconstrained position. When constrained by guide catheter 104, the distal flange portion is constrained to a smaller profile configuration.

Figure 15:
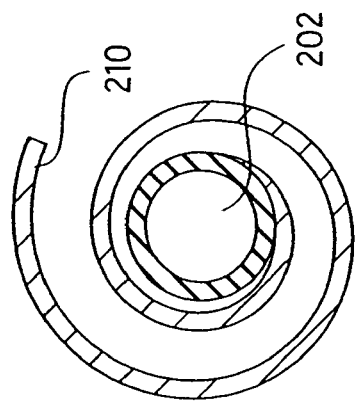
FIG. 15 is an end view of a PMR device outer tube having a ribbon spring wound around the outer tube.
Figure 14:
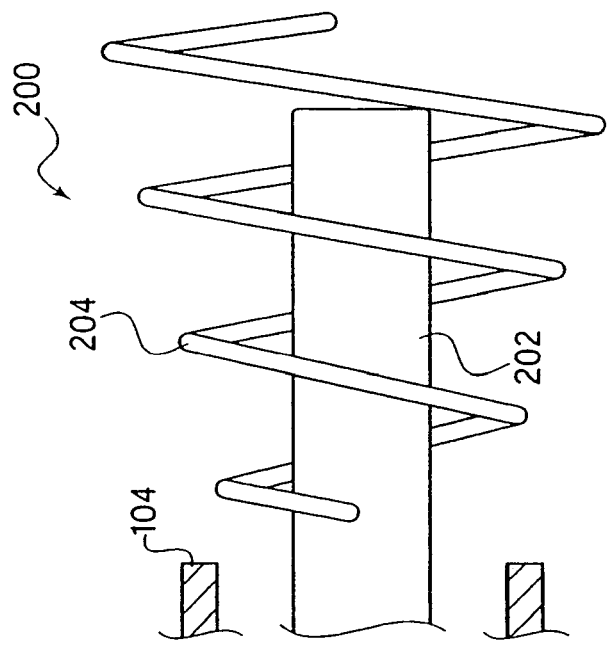
FIG. 14 is a fragmentary, longitudinal cutaway view of the PMR device outer tube of FIG. 13 extending from the guide catheter and having the spring radially expanded.
Figure 13:
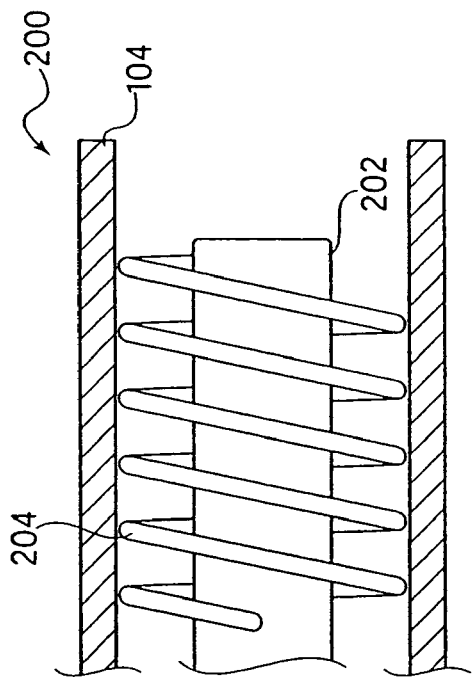
FIG. 13 is a fragmentary, longitudinal cross-sectional view of a PMR device outer tube disposed within a guide catheter and having a radially expandable distal spring constrained within the guide catheter.

FIG. 13 illustrates yet another PMR device 200. PMR device 200 includes an outer tube 202 for receiving a therapeutic catheter therethrough. Disposed about tube 202 is a spring 204 formed as a coil. Spring 204 is bonded or otherwise affixed to the outside of outer tube 202. In the embodiment shown, spring, 204 is formed as a spiral, helical coil configuration having substantially constant radial extent over the longitudinal extent of spring 204. As can be seen from inspection of FIG. 13, coil 204 is constrained within the inner wall of guide catheter 104. FIG. 13 illustrates the configuration of spring 204 prior to advancing outer tube 202 toward the heart wall. Referring now FIG. 14, PMR device 200 is illustrated after being advanced distally out of guide catheter 104. Spring 204 may be seen to have expanded to a larger radial extent or profile, and to have extended distally as well. In particular, the outer profile of spring 204 may be seen to be larger than the inner and even outer diameter of guide catheter 104. By affixing the proximal portion of spring 204 to outer tube 202, a spring having a potentially large outer profile may be wound onto an outer tube and constrained within guide catheter 104. In the embodiment illustrated, spring 204 expands radially due to the bias of the spring elements. While a preferred embodiment has a spring extending over a length of outer tube as illustrated as a helical coil or spring, other embodiments are possible. FIG. 15 illustrates other embodiment in which a spring 210 is affixed to outer tube 202 and configured as a spiral-wound ribbon wound about the outer tube. In one embodiment, spring 210 is formed in a spiral shape resembling a clock spring.

In use, after advancing spring 204 from guide catheter 104, the spring will present an enlarged distal region to prevent unwanted penetration of the heart wall by outer tube 202. After disposing spring 204 against the heart wall, a therapeutic catheter tip as previously illustrated may be advanced through tube 202 and into the heart wall. After use, spring 204 can be retracted proximally back within guide catheter 104, again reducing the profile. In some embodiments, spring 204 may be wound within guide catheter 104 by rotating outer tube 202 while retracting outer tube 202 into guide catheter 104. In other embodiments, outer tube 202 may be simply retracted into guide catheter 104. In some embodiments, designed for a single deployment of spring 204, the retraction of spring 204 into guide catheter 104 may deform the spring, reducing the elastic ability of spring 204 to expand to a large radial extent the second time. In particular, in some embodiments, after use, spring 204 may be retracted within guide catheter 104, forming an elongate very long spiral coil relative to the original relatively compact coil.

Figures 16, 17:
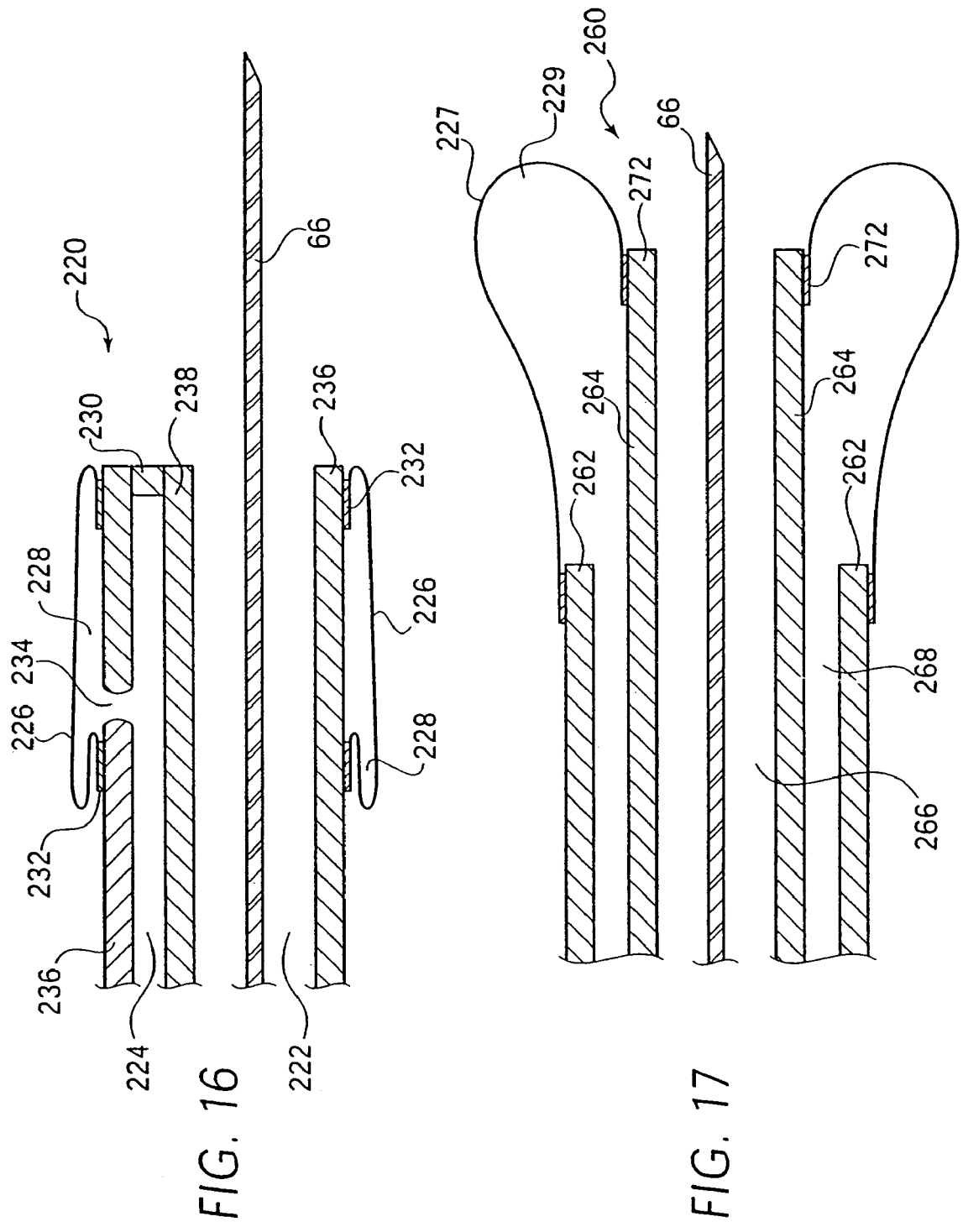
FIG. 16 is a fragmentary, longitudinal cross-sectional view of a PMR device outer tube having dual lumens and having a distal inflatable atraumatic tip.
FIG. 17 is a fragmentary, longitudinal cross-sectional view of a PMR device outer tube having coaxial lumens and having a distal inflatable atraumatic tip in an inflated configuration.

FIG. 16 illustrates a PMR device 220, including, an outer tube 236 having an internal tube wall 238 therein. Outer tube 236 includes a first lumen 222 for receiving therapeutic catheter 66. Outer tube 236 also includes a second lumen 224. The distal region of device 220 includes an inflatable balloon 226 having balloon interior 228 therein. Balloon interior 228 is in fluid communication through an inflation orifice 234 through outer tube 236 and in communication with second lumen 224 which can serve as an inflation lumen. Second or inflation lumen 224 is seen to be plugged distally by a plug 230. Balloon 226 may be seen to be bonded at 232 to outer tube 236. In use, device 222 may have balloon 226 uninflated and even pulled under vacuum to fully retract balloon 226 to a low profile configuration. Device 220 may then be disposed in a guide catheter. After being advanced to a location near the heart wall, device 220 may be advanced distally from the containing guide catheter. A suitable inflation fluid may be injected into second lumen 224 and thereafter into balloon interior 228. Balloon 226 may be expanded to attain a large distal profile for device 220. With a large profile presented, the likelihood of outer tube 236 being forced undesirably into the heart wall is greatly reduced. Once inflated, therapeutic catheter 66 may be forced against the heart wall.

Referring now FIG. 17, another embodiment of a PMR device is illustrated in a device 260 having a tip having a distal inflatable balloon. Device 260 includes inflatable balloon 227 having interior 229 affixed to an outer tube 262. Disposed within outer tube 262 is an inner tube 264, coaxially disposed within tube 262. PMR device 260 includes a first lumen 266 for receiving a therapeutic catheter, and a second or inflation lumen 268 coaxially defined between inner tube 264 and outer tube 262. Balloon 227 may be seen to be bonded at 272 to inner tube 264, and is illustrated in an inflated state.

Referring now to FIGS. 18–21, another PMR device 300 is illustrated having a shaft 301 having a distal region 302 and a distal end 304. Distal end 304 has a cross member 310 pivotally mounted at 312, where pivot mount 312 is preferably transversely disposed to the longitudinal axis of shaft 301. Cross member 310 has a first arm 311 secured to an elongate manipulation member 318. Cross member 310 has a second arm 314 having an opening or passageway 316 disposed therethrough. Shaft 301 has a first lumen 306 therethrough for receiving a therapeutic catheter and a second lumen 308 therethrough for receiving elongate cross member manipulation member 318 within.

FIG. 19 illustrates a longitudinal wafer cut through the center of device 300 and having a therapeutic inner shaft 320 disposed within first lumen 306. Opening 316 in cross member second arm 314 is positioned for receiving inner shaft 320 therethrough. As can be seen from inspection of FIG. 19, cross member 310 is disposed in a configuration oriented transversely to the longitudinal axis of device shaft 301. In this orientation, cross member 310 presents a profile or radial extent greater than the outside diameter of shaft 301. The larger profile can serve to inhibit penetration of the myocardium by shaft 301. In the embodiment illustrated, a central wall portion 322 separates first lumen 306 from second lumen 308. A spring or bias element 324 is affixed to both central wall portion 322 and cross member 310 so as to bias the cross member in a substantially transverse orientation. In embodiments having a transversely biased cross member, elongate manipulation member 318 can be a pull wire capable of being pulled for tension, but weak in compression. In embodiments not having a transverse bias for the cross member, elongate manipulation 318 is preferably sufficiently strong in compression to push the cross member to a transverse orientation. The inside diameter of second lumen 308 and elongate manipulation member 318 can be cooperatively sized to provide support in compression for the elongate manipulation member.

Figure 20:
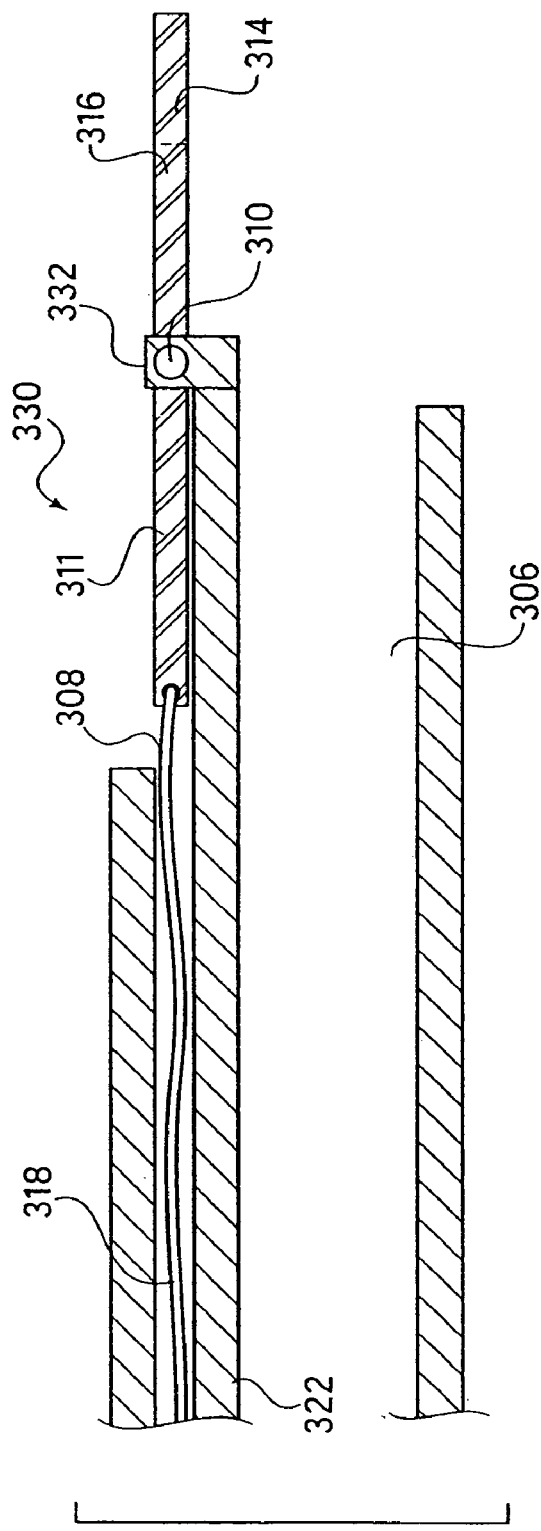
FIG. 20 is a fragmentary, longitudinal, cross-sectional view of a PMR device outer tube having a distal, atraumatic, pivotally mounted and offset cross member.
Figure 22:
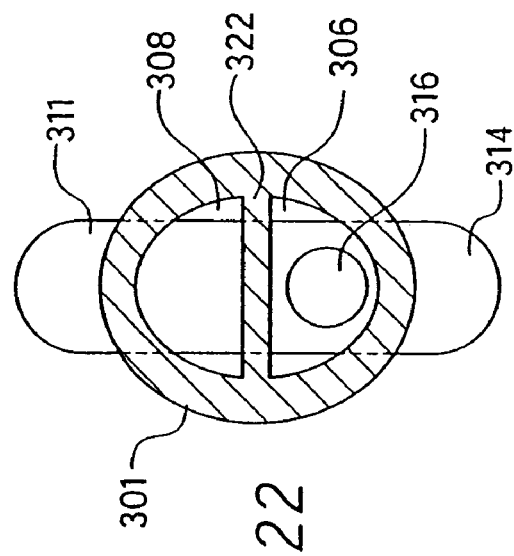
FIG. 22 is an end view of the outer tube of FIG. 19, with the cross member in a transverse position.
Figure 21:
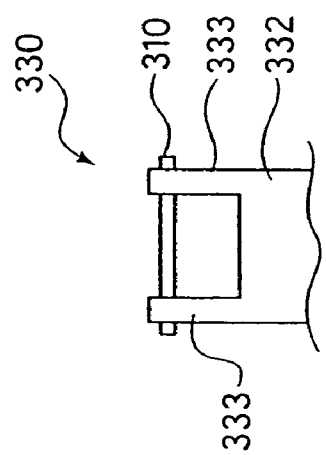
FIG. 21 is a fragmentary, top view of one possible offset mounting for the cross member of FIG. 21.

FIG. 20 illustrates a PMR device 330 similar in many respects to PMR device 300, but having cross member 310 pivotally mounted on an offset member 332 and rotatably secured to a pivot member 324. Offset member 332 can be formed of longitudinally oriented end members allowing cross member 310 to lie between the end members to achieve a substantially longitudinal orientation. As can be seen in FIG. 21, a top view of offset member 324 without having cross member 310 mounted, a pair of end members 333 can have cross member 310 mounted on pivot pin 310 between the end members. FIG. 22 illustrates a transverse cross-sectional view showing cross member 310 mounted about central wall 322 and having opening 316 therethrough.

Referring now to FIG. 23, another PMR device 350 is illustrated having an outer tube 352 having a distal end 354 and having a lumen 360 therethrough which can be used to receive a therapeutic inner shaft. Several expandable members or wings 356 are secured to outer tube 352 at distal end 354. Distal wings 356 are illustrated in a first configuration having a sufficiently small profile or radial extent to fit within an enclosing guide catheter. In one embodiment, distal wings 356 are formed of a shape memory material having a first, small radial extent at a lower temperature and a second, large radial extent at a higher temperature such as body temperature. In another embodiment, distal wings 356 are formed of a material biased to expand upon release from the constraining guide catheter. In some embodiments, distal wings 356 are formed of a metal, for example, Nitinol. In other embodiments, distal wings 356 are formed of polymeric materials. FIG. 24 illustrates a distal end view of outer tube 352 having wings 356 in a small profile configuration. FIG. 25 illustrates distal wings 356 in a second, large profile configuration.

In use, distal wings 356 can be disposed within a constraining guide catheter and advanced to a target site. Outer shaft 352 can be advanced from within the guide catheter, allowing distal wings 356 to deploy radially outward. When distal end 354 is pressed against the heart wall, wings 356 can present a larger profile object to inhibit the penetration of the distal end into the heart wall. After use, distal end 354 can be retracted back into a guide catheter. In one method, outer tube 352 is rotated as the tube is retracted within the guide catheter, urging the wings to lie close to or wrap about outer tube distal end 354. In one embodiment, the guide catheter distal end includes an internal guide groove or other structure to urge the wings to reform a curved shape about the outer tube outer wall.

Referring now to FIGS. 26–28, another PMR device 380 is illustrated having a shaft 381 having a distal region 382, a more distal, distal end 384, and a still more distal, distal-most portion 386. Shaft 381 includes a lumen 395 for receiving a shaft therethrough. Distal region 384 has several longitudinal slits or slots 388 formed through the wall of outer tube 381. Slits 388 define several wings 390 therebetween. In the embodiment illustrated, wings 390 have a region for preferential folding, such as weakened area 392. Distal end 384 is designed to longitudinally buckle under an applied force, thereby longitudinally foreshortening the distal end and radially expanding the radial extent or profile of the distal end. The applied force can come from a compressive force of being forced against the heart wall and/or a force applied by a longitudinal elongate member disposed within outer tube 381 and secured at the distal end to distal-most portion 386. In the embodiment illustrated, an inner tube 396 is slidably disposed within lumen outer tube lumen 395. Inner tube 396 has a lumen 397 therethrough for receiving a shaft with therapeutic tip. Inner tube 396 can be secured to outer tube 381 at distal-most portion 386.

FIG. 27 illustrates PMR device 380 in a radially expanded configuration in which inner tube 396 has been proximally retracted relative to outer tube 381, longitudinally foreshortening and radially expanding distal end 384. FIG. 28 illustrates an end view of PMR device 380. Wings 390 may be seen to be significantly radially expanded relative to the configuration illustrated in FIG. 26. The expanded, increased profile distal end presents a larger transverse surface area and offers an impediment to distal end 384 penetrating the heart wall.

The outer tubes and coupled atraumatic distal tips discussed are believed suitable for use in limiting unwanted penetration of the endocardium while allowing disposition within a more outer tube, for example, a guide catheter. The scope of the invention is of course not limited to these uses. The present invention can be used as part of many devices and in many applications where a small profile is desired in a first configuration and a larger profile is desired in a second configuration. Devices incorporating the present invention may be used to advantage anywhere a small distal profile is desired, including some devices used for direct passage within the body, rather than used for passage through enclosing tubes or guide catheter.

Figure 29:
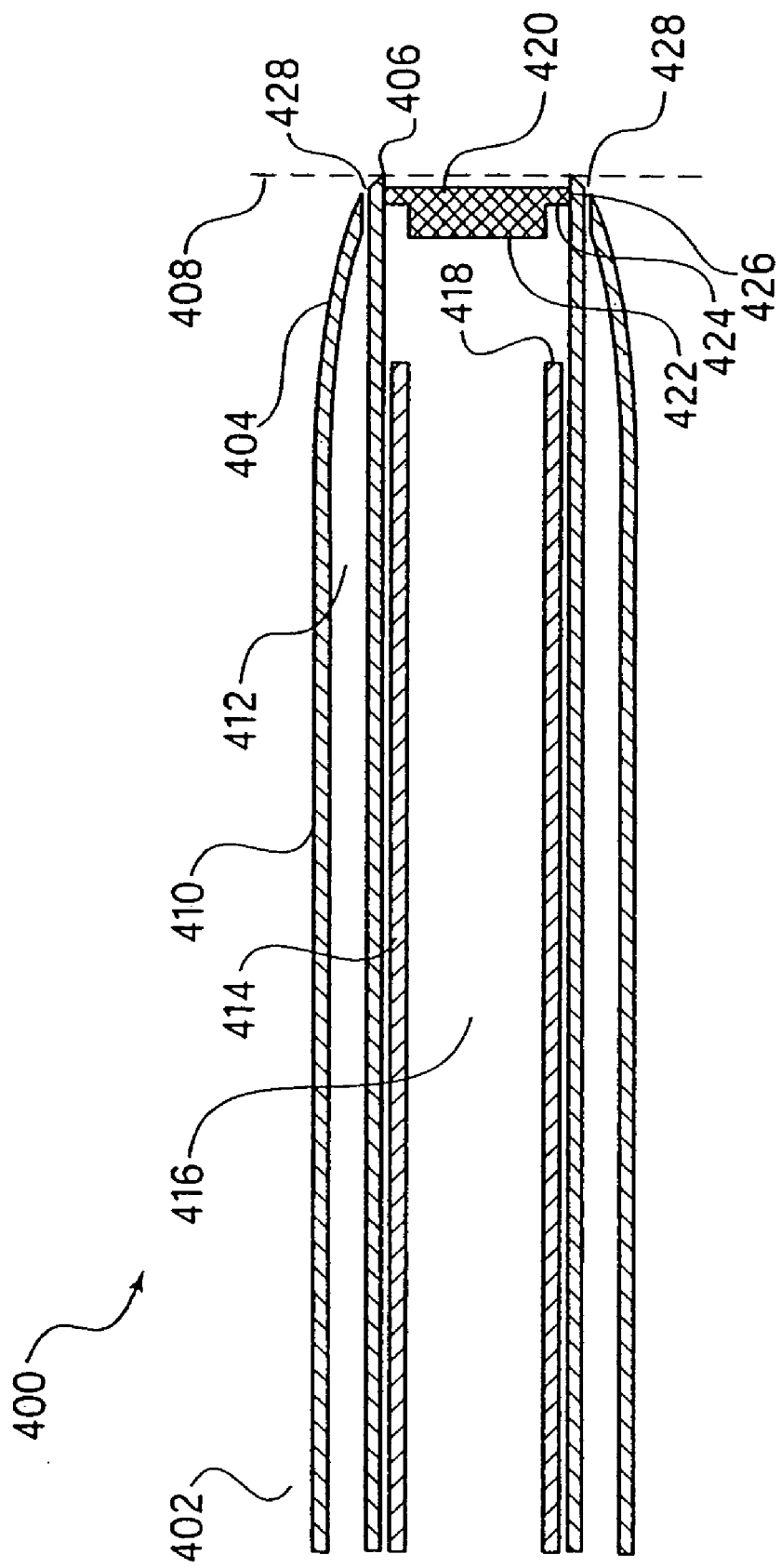
FIG. 29 is a fragmentary, longitudinal cross-sectional view of a PMR device including an inner tube, an outer tube having a lumen within the wall with a sharp distal end serving as a delivery needle, and a hood stop, the sharp distal end shown abutting the endocardium.

Referring now to FIG. 29, a PMR device 400 is illustrated, having an outer tube 410 disposed about an inner tube 414 and having a plug or hood stop 420. PMR device 420 is illustrated abutting endocardium 408. Inner tube 414 has a lumen 416 therethrough and a distal end 418, which can serve to limit the proximal travel of hood stop 420. Outer tube 410 has a distal region 404, a sharp distal tip 406, and an intermediate region 402. Outer tube 410 has a wall having a lumen 412, the space within which can serve as a therapeutic substance delivery lumen. Sharp distal end 406 can serve as a needle for injecting a therapeutic substance through distal holes 428 (shown in FIG. 31). Hood stop 420 includes a large outer diameter distal region 426, a shoulder region 424, and a small outer diameter proximal region 422. Outer tube 410 has an inside diameter in distal region 404 sufficiently large to accommodate hood stop 420, with inner tube distal end 418 serving as a stop or shoulder and having an inside diameter sufficiently small to limit the proximal travel of hood stop 429. In some embodiments, distal region 404 has a distally decreasing inside diameter, such that hood stop 420 is precluded from exiting outer tube 410 distally. In one embodiment, the stop or shoulder is formed by a region of decreased inside diameter integrally formed with the outer tube, similar to outer tube 442 of FIG. 30.

Referring now to FIG. 30, PMR device 400 is illustrated after penetrating endocardium 408. Outer tube distal end 406 has penetrated into endocardium. 408, thereby penetrating injection holes 428 (shown in FIG. 31) into the heart wall. Penetration of outer tube distal end 406 is limited by stop 420 which can now abut endocardium 408 on the distal side and abut inner tube distal end 418 on the proximal side with shoulder region 424. Outer tube wall lumen 412 can be used to inject a therapeutic substance into the heart wall through distal end 406. FIG. 31 illustrates an end view of PMR device 400, illustrating injection holes 428 in outer tube distal end 406, distal stop 420, and outer tube 410. Outer tube 410 and inner tube 414 can be formed of materials previously discussed, for example hypotube or polymeric materials.

Figure 32:
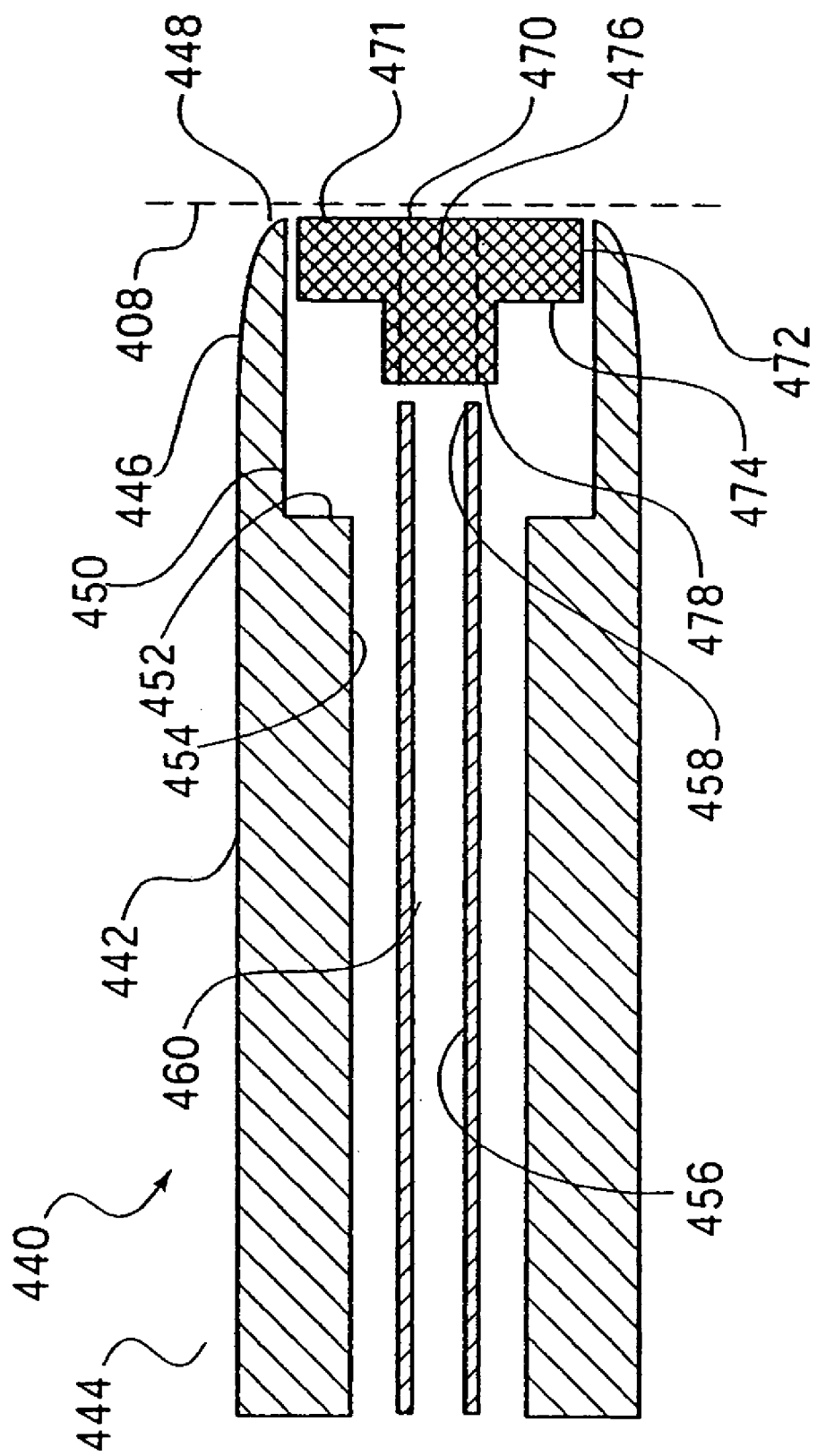
FIG. 32 is a fragmentary, longitudinal cross-sectional view of a PMR device including an inner tube having a delivery lumen within, an outer tube having a lumen within the wall with a sharp distal end serving as a penetrating needle, and a hood stop, the sharp distal end shown abutting the endocardium.
Figure 33:
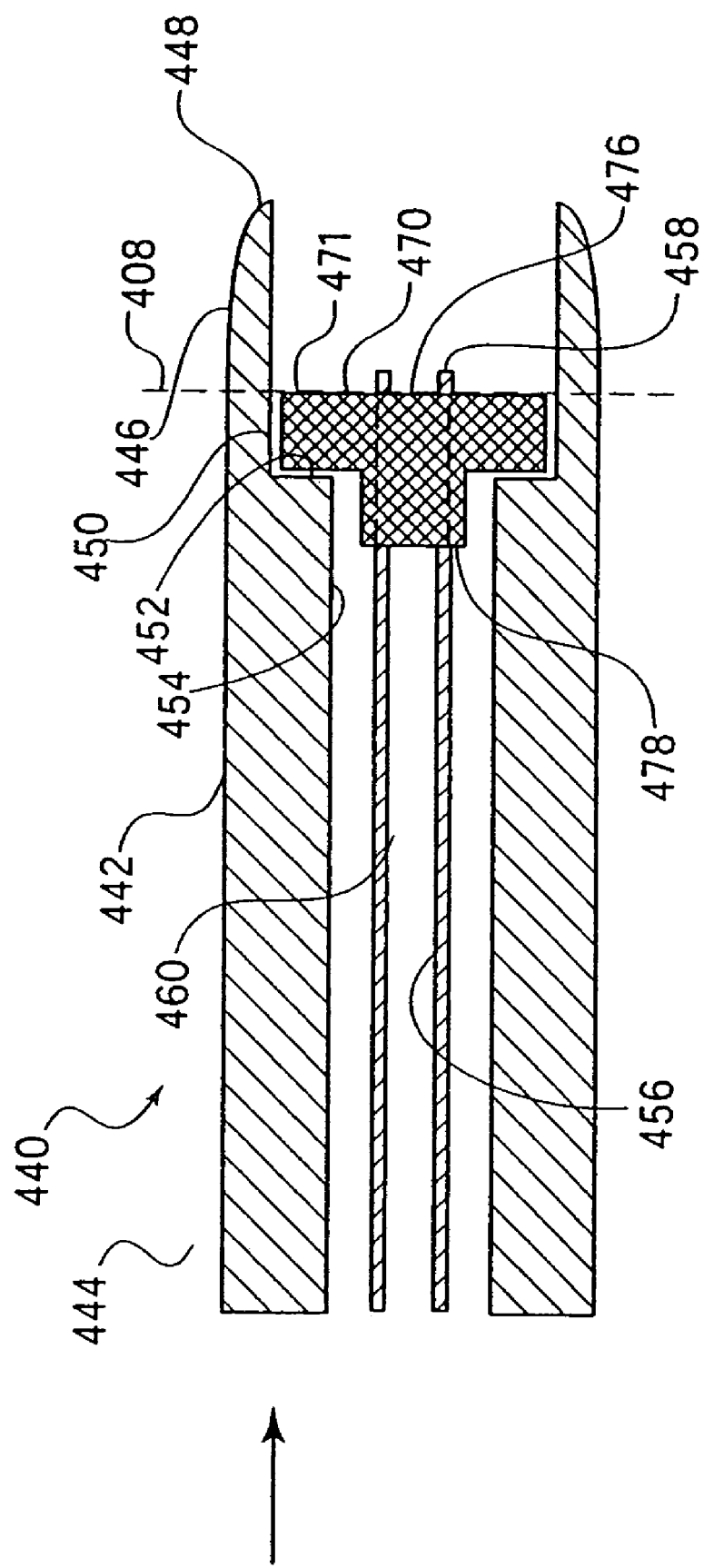
FIG. 33 is a fragmentary, longitudinal cross-sectional view of the PMR device of FIG. 32, the sharp distal end shown penetrating the endocardium up to the hood stop now abutting an inner shoulder within the outer tube.

Referring now to FIG. 32, a PMR device 440 is illustrated, having a outer tube 442, an inner tube 456, and a plug or hood stop 470. PMR device 440 is illustrated abutting endocardium 408. Inner tube 456 has a distal end 458 and a delivery lumen 460 within. In some embodiments, distal end 458 is sharp and has a length intended to penetrate into the heart wall through hood stop 470. In other embodiments, distal end 458 is dull and has a length intended to remain within hood stop 470 when the PMR device has penetrated into the heart wall. Delivery lumen 460 can be used to inject or infuse a therapeutic substance. Outer tube 442 includes a sharp distal tip 448, a distal region 446, and an intermediate region 444. Outer tube 442 includes a shoulder region 452 disposed proximal of a larger inside diameter region 450 and distal of a smaller inside diameter region 454. Hood stop 470 includes a distal large outer diameter region 472, an annular ring portion 471, a shoulder region 474, and a proximal small outer diameter region 478. Hood stop 470 can also include a lumen 476 extending through the stop, allowing some penetration of inner tube distal end 458 past the distal face of the stop and into the heart wall, to aid in injecting a therapeutic substance into the heart wall. In some embodiments, distal region 446 has a distally decreasing inside diameter, such that hood stop 470 is precluded from exiting outer tube 442 distally.

Inner tube lumen 460 can be used to inject a therapeutic substance into the heart wall past distal end 458. Outer tube 442 and inner tube 456 can be formed of materials previously discussed, for example hypotube or polymeric materials. Hood stop 470 can be formed of atraumatic polymeric materials, previously discussed.

Figure 34:
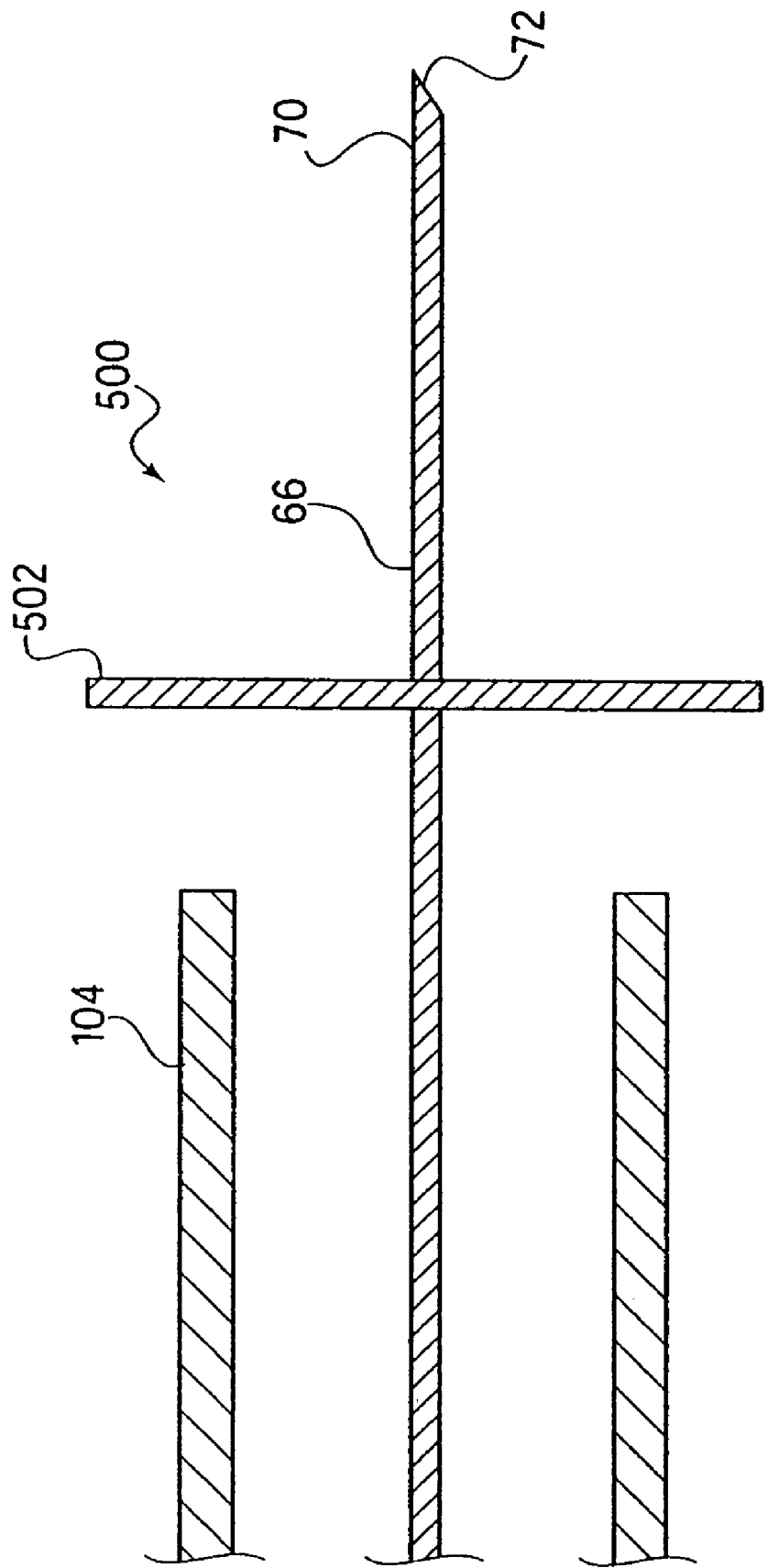
FIG. 34 is a fragmentary, longitudinal cross-sectional view of a PMR device inner shaft having a flexible atraumatic flange stop, illustrated after being distally extended from a guide catheter.

Referring now to FIG. 34, a PMR device 500 is illustrated disposed within guide catheter 104, having inner tube or shaft 66 with therapeutic tip region 70 and terminating in cutting tip 72, as discussed with respect to FIG. 2. PMR device 500 also has a flange or stop 502, which can be similar to flange 168 as discussed with respect to FIGS. 7 and 8. Flange 502 can be formed of the same materials discussed with respect to flange 168 of FIGS. 7 and 8. Flange 502 is preferably formed of an elastomeric material, which contracts or is folded back, such that the flange has a radial extent or profile small enough to fit within guide catheter 104. Guide catheter 104 can be advanced to be near a target site, with flange 502 folded within guide catheter 104. Inner shaft 66 can be advanced forward relative to guide catheter 104, thereby deploying flange 502 to an expanded state having an increased radial extent or profile. Inner shaft 66 is preferably fixedly attached to flange 502. As inner shaft cutting, tip 72 is advanced into the myocardium, flange 502 can serve to limit the extent of travel into the heart wall. After use, flange 502 can be retracted into guide catheter 104, reducing the radial extent of flange 502, and guide catheter 502 can be used further or retracted from the body.

Figure 35:
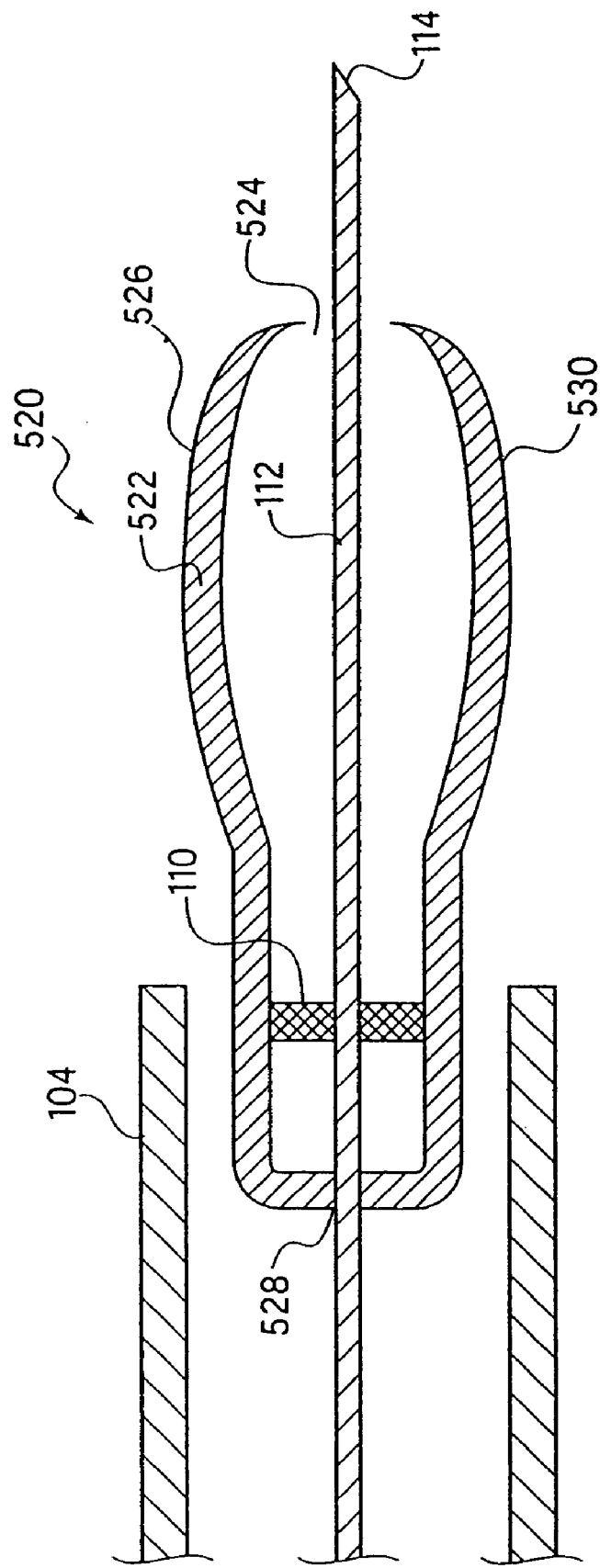
FIG. 35 is a fragmentary, longitudinal cross-sectional view of a PMR device inner shaft having an expandable atraumatic spring stop, illustrated prior to being distally extended from a guide catheter.

Referring now to FIG. 35, a PMR device 520 is illustrated, advanced distally from guide catheter 104. PMR device 520 includes inner shaft or therapeutic catheter 112 terminating in cutting tip 114, discussed previously with respect to FIGS. 3 and 4. PMR device 520 includes a bulbous tip or hood 530 having an outer wall 522 and a distal region 526 terminating in a distal orifice 524. Outer wall 522 can be formed of the same materials as outer wall 102 discussed with respect to FIGS. 3 and 4. Bulbous tip 530 can be fixedly attached to inner shaft 112 through flange 110 and at a bulbous tip proximal region 528. Bulbous tip 530 is illustrated as having been distally extended from guide catheter 104.

In use, cutting tip 114 can penetrate into the myocardium, with the depth of penetration limited by bulbous tip distal region 526 expanding upon contact with the endocardium. In operation, outer wall 522 can operate much the same as outer wall 102 illustrated in FIG. 4, expanding upon contact with the heart chamber wall. After use, bulbous tip 530 can be retracted into guide catheter 104. In one embodiment, PMR device 520 has a shorter tube enclosing the inner shaft distal region relative to that of PMR device 100. In one embodiment, PMR device 530 has inner shaft 112 directly disposed within guide catheter 104 for a majority of the length of inner shaft 112.

Figure 36:
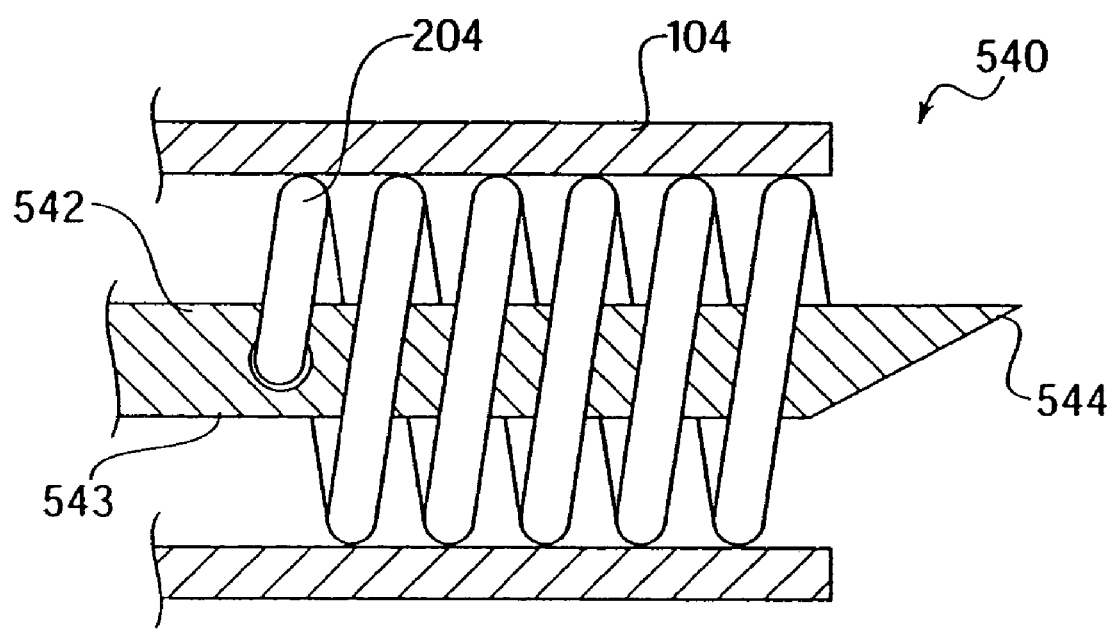
FIG. 36 is a fragmentary, longitudinal cross-sectional view of a PMR device within a guide catheter.

Referring now to FIG. 36, a PMR device 540 is illustrated disposed within guide catheter 104. PMR device 540 includes an inner shaft 542 terminating in a distal therapeutic and/or cutting tip 544 having expandable coil 204 secured to inner shaft 542 at a fixation location 543 located proximal of a cutting tip 544. Coil 204 was discussed previously with respect to FIGS. 13 and 14. Inner shaft 542 can be formed of similar materials as inner shaft 112 discussed with respect to FIG. 3. FIG. 36 illustrates coil 204 constrained within guide catheter 104.

In use, guide catheter 204 can be advanced to near a target site, with PMR device coil 204 constrained within guide catheter 104. Inner shaft 542 can be distally advanced, or guide catheter 103 proximally retracted, freeing coil 204, allowing the coil to expand radially, as illustrated and discussed with respect to FIGS. 13 and 14. Coil 204 can act to limit the penetration of cutting tip 544 into the myocardium. After penetration into the myocardium, coil 204 can be retracted into the guide catheter. In some methods, inner shaft 542 is rotated to aid in bringing coil 204 within guide catheter 204.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. An elongate medical device for performing medical procedures on a patient comprising:
    a first member having a distal end and an outer surface,
        the first member also having a first lumen and a second lumen,
        the first member having an elongated configuration wherein the length of the first member is at least ten times greater than the width of the first member;
    a second member pivotally coupled to the first member at a pivot area of the first member,
        the second member having a first region on one side of the pivot area and a second region on a different side of the pivot area,
            the second region of the second member having an opening therethrough,
                the opening aligned with either the first lumen or the second lumen of the first member; and
    a manipulation member extending through either the first lumen or the second lumen,
        the manipulation member mechanically coupled to the second member.

2. The elongate medical device of claim 1, wherein the manipulation member is a line positioned within the second lumen of the first member.

3. The elongate medical device of claim 1, wherein the first member defines a recess sized to accept at least a portion of the second member when the second member is pivoted into an open position by the manipulation member.

4. The elongate medical device of claim 1, wherein the pivot area of the first member is positioned in the distal end of the first elongated member.

5. The elongate medical device of claim 4 wherein the distal end of the first member has a distal most region and wherein the pivot area of the first elongated member is positioned in the distal most region.

6. The elongate medical device of claim 1 further comprising:
   a third member,
      the third member slidably positioned within the first lumen of the first member, the third member having a piercing tip.

7. The elongate medical device of claim 6 wherein the third member has an internal lumen and may be slid within the first lumen to extend the piercing tip from the distal end of the first member.

8. The elongate medical device of claim 7 wherein the third member is positioned to slide through the opening of the second member when the second member is in a first position.

9. The elongate medical device of claim 1 wherein the second member may be pivoted such that it is parallel to a longitudinal axis of the first member.

10. The elongate medical device of claim 1 wherein the second member may be pivoted such that it is perpendicular to a longitudinal axis of the first member.

11. The elongate medical device of claim 1 wherein the pivot area comprises a pivot pin and channel supporting the pivot pin.

12. The elongate medical device of claim 1 wherein the first region and the second region of the second member have symmetrical perimeter shapes.

13. The elongate medical device of claim 1 wherein the second member may be manipulated with the manipulation member from a proximal end of the first member.

14. The elongate medical device of claim 1 wherein the first lumen and the second lumen of the first member are symmetrical about a longitudinal axis of the first member.

* * * * *